US011389312B2

(12) United States Patent
Alvarez et al.

(10) Patent No.: US 11,389,312 B2
(45) Date of Patent: Jul. 19, 2022

(54) STENTS WITH INCREASED FLEXIBILITY

(71) Applicant: SINTRA MEDICAL LLC, Miami, FL (US)

(72) Inventors: Carlos Gabriel Alvarez, Monterrey (MX); Jesus Romo Rico, Monterrey (MX)

(73) Assignee: Sintra Medical LLC, Miami, FL (US)

( * ) Notice: Subject to any disclaimer, the term of this patent is extended or adjusted under 35 U.S.C. 154(b) by 28 days.

(21) Appl. No.: 16/962,242

(22) PCT Filed: Jan. 16, 2019

(86) PCT No.: PCT/US2019/013843
§ 371 (c)(1),
(2) Date: Jul. 15, 2020

(87) PCT Pub. No.: WO2019/143717
PCT Pub. Date: Jul. 25, 2019

(65) Prior Publication Data
US 2021/0059845 A1 Mar. 4, 2021

Related U.S. Application Data

(60) Provisional application No. 62/618,007, filed on Jan. 16, 2018.

(51) Int. Cl.
A61F 2/915 (2013.01)
A61F 2/07 (2013.01)
A61F 2/958 (2013.01)

(52) U.S. Cl.
CPC .............. A61F 2/915 (2013.01); A61F 2/958 (2013.01); A61F 2002/072 (2013.01); A61F 2002/91575 (2013.01); A61F 2210/0014 (2013.01); A61F 2230/0013 (2013.01); A61F 2230/0019 (2013.01); A61F 2230/0026 (2013.01); A61F 2230/0045 (2013.01)

(58) Field of Classification Search
CPC ...... A61F 2230/0045; A61F 2230/0026; A61F 2/915; A61F 2002/91575
See application file for complete search history.

(56) References Cited

U.S. PATENT DOCUMENTS

| 5,913,895 A | 6/1999 | Burpee et al. |
| 6,258,116 B1 | 7/2001 | Hojeibane |
| 2002/0165605 A1* | 11/2002 | Penn ................ A61F 2/915 623/1.15 |
| 2003/0125800 A1* | 7/2003 | Shulze ................ A61P 17/02 623/1.15 |
| 2006/0058870 A1 | 3/2006 | Iki et al. |

(Continued)

FOREIGN PATENT DOCUMENTS

| EP | 1151730 B1 | 1/2007 |
| EP | 2638882 A1 | 9/2013 |

(Continued)

Primary Examiner — Rebecca S Preston
(74) Attorney, Agent, or Firm — Shay Glenn LLP

(57) ABSTRACT

Stents that are adapted to be balloon expanded and include adjacent supports connected by connecting portions. The configurations, materials, and/or dimensions of at least one of the supports and connection portions allows the stents to be expanded to a greater extent, and optionally with reduced foreshortening.

20 Claims, 18 Drawing Sheets

(56) References Cited

U.S. PATENT DOCUMENTS

| | | |
|---|---|---|
| 2006/0095113 A1 | 5/2006 | Niermann |
| 2009/0036974 A1 | 2/2009 | Penn |
| 2009/6105809 | 4/2009 | Lee et al. |
| 2011/0190861 A1 | 8/2011 | Pericevic et al. |
| 2011/0238157 A1 | 9/2011 | Li et al. |
| 2012/0310363 A1 | 12/2012 | Gill et al. |
| 2013/0178928 A1 | 7/2013 | Vyas et al. |

FOREIGN PATENT DOCUMENTS

| | | |
|---|---|---|
| EP | 2881089 A1 | 6/2015 |
| WO | WO2011/032526 A1 | 3/2011 |
| WO | WO2014/176361 A1 | 10/2014 |

\* cited by examiner

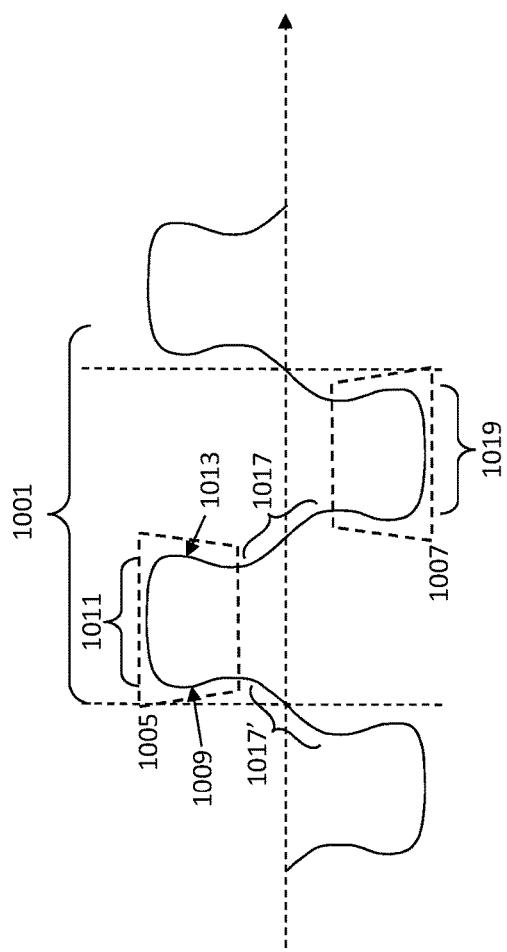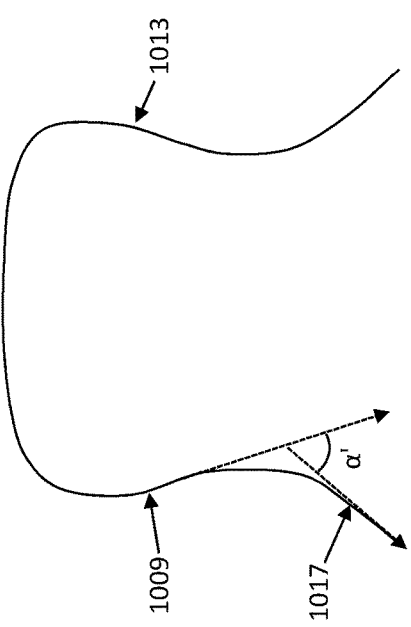

| Stent Graft 5 x 18 mm | |
|---|---|
| Initial length | 17.95 mm |
| Initial diameter | 2.107 mm |
| Final diameter with balloon | 5.490 mm |
| Final diameter 30s after balloon removed | 5.007 mm |
| Final length | 17.70 mm |
| Recoil (%) | 8.8% |
| Foreshortening (%) | 1.4% |

FIG. 18A

| Stent Graft 5 x 38 mm | |
|---|---|
| Initial length | 38.06 mm |
| Initial diameter | 2.217 mm |
| Final diameter with balloon | 5.210 mm |
| Final diameter 30s after balloon removed | 4.900 mm |
| Final length | 37.73 mm |
| Recoil (%) | 5.9 % |
| Foreshortening (%) | 0.87 % |

FIG. 18B

| Stent Graft 6 x 18 mm | |
|---|---|
| Initial length | 17.62 mm |
| Initial diameter | 2.207 mm |
| Final diameter with balloon | 5.747 mm |
| Final diameter 30s after balloon removed | 5.303 mm |
| Final length | 17.11 mm |
| Recoil (%) | 7.7 % |
| Foreshortening (%) | 2.9 % |

FIG. 18C

| Stent Graft 6 x 38 mm | |
|---|---|
| Initial length | 37.81 mm |
| Initial diameter | 2.357 mm |
| Final diameter with balloon | 6.277 mm |
| Final diameter 30s after balloon removed | 5.907 mm |
| Final length | 35.83 mm |
| Recoil (%) | 5.9 % |
| Foreshortening (%) | 5.2 % |

FIG. 18D

STENTS WITH INCREASED FLEXIBILITY

CROSS REFERENCE TO RELATED APPLICATIONS

This patent application claims priority to U.S. patent application No. 62/618,007, filed on Jan. 16, 2018, titled "STENTS WITH INCREASED FLEXIBILITY", and herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are expandable intraluminal grafts ("stents") for use within a body passageway or duct which are particularly useful for repairing blood vessels narrowed or occluded by disease. The stents described herein are configured to change size over a large range, while minimizing the strain on the stent.

BACKGROUND

Intravascular stents may be used in coronary arteries and other body lumens of human patients. Stents are generally tubular-shaped devices which function to hold open a segment of a blood vessel or other body lumen such as a coronary artery. They also are suitable for use to support and hold back a dissected arterial lining that can occlude the fluid passageway. At present, there are numerous commercial stents being marketed throughout the world. For example, prior art stents typically have multiple cylindrical rings connected by one or more connecting links. While some of these stents are flexible and have the appropriate radial rigidity needed to hold open a vessel or artery, there typically is a tradeoff between flexibility and radial strength and the ability to tightly compress or crimp the stent onto a catheter so that it does not move relative to the catheter or dislodge prematurely prior to controlled implantation in a vessel.

Intravascular stents are known and there are numerous structural designs in commercial use. One well known structural pattern includes a tubular stent having rings connected by links. Typically, there are two or more links connecting adjacent rings. While stents having two links between adjacent rings (two-link stents) offer the benefit of low crimp profile and high flexibility, these benefits come with a trade-off in terms of longitudinal stability. Further, peak-to-peak stent patterns (in which the peaks on adjacent rings point toward each other and are essentially axially aligned) offer dense packing of stent rings, which in turn allows for a stent pattern with high radial strength and high radial stiffness. One stent pattern that incorporates these design features is the 2 link offset peak-to-peak style stent. While this stent pattern performs well in terms of traditional stent metrics, it experiences one key tradeoff, namely it will excessively shorten under modest longitudinal compressive loads.

Two-link stents, specifically offset peak-to-peak, where the peaks of adjacent rings point toward each other but are slightly offset circumferentially, excessively shorten under modest (clinically relevant) longitudinal compressive loads. This creates unwanted implications for safety and efficacy of the stent implant. Offset and angled link designs lend readily to collapse behavior, as links do not provide resistance in direction of load, and in addition offset link designs create a bending moment effect, which encourages the bar arms adjacent to link structures to bend and swing excessively (stress is focused in these bar arms).

SUMMARY OF THE DISCLOSURE

The present disclosure relates to stents, such as balloon-expandable vascular prosthesis. In addition to vascular applications, these devices may be used for tracheal, bronchial patency and/or in iliac or renal arteries.

The stents described herein have greater flexibility than prior art stents and expand with less foreshortening, based in part upon a combination of factors, including the configuration of one or more portions of the stent, material properties, and dimensions of one or more portions of the stents.

The stents can include a plurality of annular supports (rings) that are adjacent and extend transversely (e.g., at 90 degrees, but including +/− 15 degrees) to the longitudinal distal-to-proximal axis of the device. The rings may be coupled together by a connecting portion, which can include one or more connectors (and in particular, omega-shaped connectors).

At least some of the supports (e.g., rings) may have a configuration that has a repeating pattern (e.g., a biphasic pattern) of a pair of flat-ended, open trapezoidal shapes (which may be rounded at the corners) that are circumferential offset but face each other and may be connected at their ends by connecting members that may be straight or curved (e.g., S-shaped). The trapezoidal shapes may be square, rectangular, isosceles (e.g., a wide-mouthed isosceles in which the open end of the trapezoid would be the longer parallel side, or narrow-mouthed isosceles, in which the open end of the trapezoid would be the shorter parallel side).

Typically, as the stent device is expanded, the flat end of the open trapezoidal shapes stay approximately the same (e.g., same length, and may remain substantially parallel with each other), while the connecting members may bend relative to the flat ends. In some variations, the legs of the open trapezoidal shapes (the legs forming the open ends) may bend relative to the connecting members and/or the flat end(s).

As mentioned, the connectors may be configured as omega connectors, which may include an arc region (e.g., semi-circular or 180 degree arc, 170 degree arc, 190 degree arc, 200 degree arc, 210 degree arc, etc.) from which a pair of straight legs may extend from either side of the ends of the arc region, e.g., in a single line. For example, each omega-shaped connector may include includes an arc region and a pair of linear sections extending from the arc regions on either side of the arc region. One or both ends of the connector may be L-shaped. For example, the omega connector may include a first an L-shaped end connecting to the second side of one of the first open trapezoidal portions of the plurality of biphasic cells and a second L-shaped end connecting to the fifth side of one of the second open trapezoidal portions of the plurality of biphasic cells.

In general, the apparatuses described herein may be configured as balloon-expandable stent grafts that may be used in percutaneous transluminal angioplasty (PTA) procedures, including in particular in peripheral arteries such as tibial, femoral and iliac. Balloon-expandable stents are Endovascular prostheses and may be metallic tubular meshes that expand radially by means of inflation of a balloon. The stent grafts describe here may have a frame (e.g., a cobalt chrome tubular frame/mesh, Nitinol tubular frame/mesh, stainless steel tubular frame/mesh, etc.), embedded into sleeve formed from a polymer matrix. The sleeve may be porous.

For example, this apparatuses and methods described herein relate to stent grafts ("stents") having radiused struts that may be embedded and/or enveloped in a polymer matrix. The stent graft may comprise rings that form radiused struts in sinusoidally ("s-shaped") shaped segments. The rings may be connected by omega-shaped crosslinks, e.g., connectors or crosslinks that may have an omega ($\Omega$) shape. The stent struts may be embedded and/or enveloped into a polymer matrix of a composite, such as a composite of ePTFE that may enhance its mechanical properties. The improved properties may permit the stent to go through tortuous paths of injured peripheral arteries with the required flexibility and with the proper radial stability to open the vascular vessel and recover the blood flow.

For example, described herein are stent devices having a length extending in a distal to proximal direction, the device comprising: a plurality of adjacent rings arranged transverse to a length of the device, wherein each ring is a ring comprising length of material arranged radially around the length of the stent device as a plurality of repeating biphasic cells, each biphasic cell comprising a first open trapezoidal portion having a first side, a second side and a third side forming a proximal-facing opening, and a second open trapezoidal portion having a fourth side, a fifth side and a sixth side forming a distal-facing opening, wherein the second side and the fifth side are parallel, further wherein the third side of the first open trapezoidal portion is connected to the fourth side of the second open trapezoidal portion by a first connector region extending at a first angle relative to the third side, and wherein the first side of the first open trapezoidal portion connects to a sixth side of an adjacent biphasic cell in the ring by a second connector extending at a second angle relative to the first side; and a plurality of omega-shaped connectors connecting each ring that is adjacent to a more distal ring to the more distal ring, wherein each omega-shaped connector connects the second side of one of the first open trapezoidal portions of the plurality of biphasic cells in the ring that is adjacent to the more distal ring to the fifth side of one of the second open trapezoidal portions of the plurality of biphasic cells of the more distal ring; wherein the stent device has a first configuration in which the plurality of adjacent rings have a first diameter, and the stent device has a second configuration in which the plurality of adjacent rings have a second diameter that is greater than the first diameter, and wherein the second side and the first side remain parallel as the stent device is expanded from the first configuration to the second configuration.

A stent device having a length extending in a distal to proximal direction may include: a plurality of adjacent rings arranged transverse to a length of the device, wherein each ring is a ring comprising length of material arranged radially around the length of the stent device as a plurality of repeating biphasic cells, each biphasic cell comprising a first open trapezoidal portion having a first side, a second side and a third side forming a proximal-facing opening, and a second open trapezoidal portion having a fourth side, a fifth side and a sixth side forming a distal-facing opening, wherein the second side and the fifth side are parallel, further wherein the first open trapezoidal portion is radially offset from the second open trapezoidal portion and the third side of the first open trapezoidal portion is connected to the fourth side of the second open trapezoidal portion by a first connector region extending at a first angle relative to the third side, and wherein the first side of the first open trapezoidal portion connects to a sixth side of an adjacent biphasic cell in the ring by a second connector extending at a second angle relative to the first side; and between one and three omega-shaped connectors connecting each ring that is adjacent to a more distal ring to the more distal ring, wherein each omega-shaped connector connects the second side of one of the first open trapezoidal portions of the plurality of biphasic cells in the ring that is adjacent to the more distal ring to the fifth side of one of the second open trapezoidal portions of the plurality of biphasic cells of the more distal ring, further wherein an omega-shape of each of the omega-shaped connectors connecting the plurality of adjacent rings is oriented in the same distal to proximal direction; wherein the stent device has a first configuration in which a first diameter of the plurality of adjacent rings is between 0.5 mm and 4 mm and a second configuration in which a second diameter of the plurality of adjacent rings is between 3 mm and 7 mm, and wherein the second side and the first side remain parallel but the first and second angles change as the stent device expands from the first configuration to the second configuration.

As mentioned, the plurality of omega-shaped connectors may comprises between 1 and 3 omega-shaped connectors. In some variations, the plurality of omega-shaped connectors has a maximum of 2 omega-shaped connectors.

Typically, the first open trapezoidal portion (or at least the flattened top of the open trapezoidal portion) is radially offset from the second open trapezoidal portion (e.g., the flattened top of the open trapezoidal portion). This offset may increase as the device transitions from the first (unexpanded configuration) into the second (expanded) configuration, while the flattened top remains essentially the same shape and size. Thus, the radial offset between the first open trapezoidal portion and the second open trapezoidal portion may increase as the stent device transitions from the first configuration to the second configuration.

In general, the length of any of the devices described herein may be between about 10 mm and about 40 mm (e.g., between about 12 mm and about 39 mm, between about 12 mm and 38 mm, e.g., 40 mm or less, 39 mm or less, 38 or less, etc.). The first diameter (e.g., the outer diameter of each ring in the un-expanded configuration) may be between about 0.5 mm and about 4 mm and the second diameter (e.g., the outer diameter of the rings in the expanded configuration) may be between about 3 mm and about 7 mm.

The frame (e.g., the length of material) may comprises one or more of: an alloy of chromium cobalt, a nickel titanium alloy (e.g., Nitinol), a stainless steel and a magnesium alloy.

Any of these devices may include a sleeve bonded to and/or encapsulating the frame (e.g., the plurality of connected rings). The sleeve may be a polymeric matrix in which the plurality of rings is encapsulated. For example, the sleeve may be ePTFE. The sleeve material may be electrospun onto the frame. The sleeve may comprise a porous material. In some variations, the sleeve may have a thickness of between about 0.005 and 0.001 inches.

In any of the stent devices described herein the omega connectors may be oriented so that an omega-shape (the approximately "$\Omega$" shape) of each of the omega-shaped connectors connecting the plurality of adjacent rings are all in the same distal to proximal direction, e.g., so that they all face distally or proximally.

As mentioned above, the first open trapezoidal portion may be an open rectangle, open isosceles trapezoid, etc. The open trapezoidal portions (first and second) may generally include a flattened end with square or rounded corners extending into a pair of legs. The legs forming the open end may be straight or curved (including sinusoidal). The legs may bend as the device expands from the first (un-expanded) to the second (expanded) configuration. In some variations the second open trapezoidal portion may be the same shape as the first open trapezoidal shape, or different. For example, the first and third sides may be parallel and in some variations the fourth and sixth sides are not parallel. The first and second open trapezoidal shapes have opposite open ends that face different each other (e.g., one faces distally while the other faces proximally). Either or both the first open trapezoidal portion and the second open trapezoidal portion may have rounded edges.

The width of the length of material forming the repeating biphasic cells (the rings) may be constant or it may vary. For example, the width may be between about 0.05 and about 0.5 mm (e.g., between about 0.1 and about 0.3, between about 0.1 and about 0.2, etc.).

The plurality of adjacent rings are typically separated from each other by a ring offset. The connector (e.g., the omega-shaped connector) may sit within this ring offset. The ring offset may be a distance of between 0.1 and 1 mm (e.g., between about 0.1 mm and about 0.8 mm, between about 0.1 mm and 0.6 mm, etc.) along the distal to proximal length of the stent device. In general, the distal to proximal height of each ring may be between about 0.5 mm and about 4 mm (e.g., between about 0.5 mm and about 3.5 mm, between about 1 mm and about 3 mm, etc.).

The stent devices described herein, because of the dimensions and arrangement of the frame (e.g., the repeating biphasic cell configuration) and the connectors (e.g., the omega-shaped connectors) may permit the device to have particularly advantageous properties, including resistance to kinking. For example, the stent device may bend at least 90 degrees along its length in the first configuration without kinking. The device may foreshortens less than 7% (e.g., less than 6%, less than 5.5%, etc.) when expanding from the first configuration to the second configuration. For example, the device may foreshorten less than 7% (e.g., less than 6%, less than 5.5%, etc.) when the second diameter of the plurality of adjacent rings is greater than 2.9 times the first diameter of the plurality of adjacent rings.

The first open trapezoidal portions of the repeating biphasic cells in each of the rings may be aligned with the first open trapezoidal portions in the other rings along the proximal to distal length of the device. Similarly the second open trapezoidal portion of the repeating biphasic cells may be aligned with each other along the length (proximal to distal) of the device.

The patterns forming the rings may alternatively be described herein as a repeating pattern of alternating flattened tops and flattened bottoms, wherein the flattened tops extend transverse to the length of the device and wherein the flattened bottoms extend transverse to the length of the device and further wherein the flattened tops and flattened bottoms are connected by sigmoidal-shaped connectors so that each flattened top forms part of a distal-facing U-shape and each flattened bottom forms part of a proximal-facing U-shape. Each flattened top and a portion each of two sigmoidal-shaped connectors to which it is attached may form a first open trapezoidal portion having a proximal-facing opening and each flattened top and a portion each of two sigmoidal-shaped connectors to which it is attached forms a second open trapezoidal portion having a distal-facing opening.

Thus, described herein are stent device comprising: a plurality of adjacent rings arranged transverse to a length of the device in a proximal to distal direction, wherein each ring comprises a length of material arranged radially around the length of the stent device in a repeating pattern of alternating flattened tops and flattened bottoms, wherein the flattened tops extend transverse to the length of the device and wherein the flattened bottoms extend transverse to the length of the device and further wherein the flattened tops and flattened bottoms are connected by sigmoid-shaped connectors so that each flattened top forms part of a distal-facing U-shape and each flattened bottom forms part of a proximal-facing U-shape; a plurality of omega-shaped connectors connecting each ring that is adjacent to a more distal ring to the more distal ring, wherein each omega-shaped connector connects one of the flattened tops the ring that is adjacent to the more distal ring to a flattened bottom of the more distal ring; wherein the stent device has a first configuration in which the plurality of adjacent rings have a first diameter, and the stent device has a second configuration in which the plurality of adjacent rings have a second diameter that is greater than the first diameter, and wherein the flattened tops and the flattened bottoms remain parallel to each other as the stent device is expanded from the first configuration to the second configuration.

The plurality of omega-shaped connectors may comprise between 1 and 3 omega-shaped connectors. The plurality of omega-shaped connectors may have a maximum of 2 omega-shaped connectors. The flattened tops of each ring may be radially offset from the flattened bottoms. The radial offset may increase as the stent device transitions from the first configuration to the second configuration. As mentioned above, an omega-shape of each of the omega-shaped connectors connecting the plurality of adjacent rings may be oriented in the same proximal to distal direction.

For example, a stent device may include: a plurality of adjacent rings arranged transverse to a length of the device in a proximal to distal direction, wherein each ring comprises a length of material arranged radially around the length of the stent device in a repeating pattern of alternating flattened tops and flattened bottoms, wherein the flattened tops extend transverse to the length of the device and wherein the flattened bottoms extend transverse to the length of the device and further wherein the flattened tops and flattened bottoms are connected by sigmoidal-shaped connectors so that each flattened top forms part of a distal-facing U-shape and each flattened bottom forms part of a proximal-facing U-shape; between one and three omega-shaped connectors connecting each ring that is adjacent to a more distal ring to the more distal ring, wherein each omega-shaped connector connects one of the flattened tops the ring that is adjacent to the more distal ring to a flattened bottom of the more distal ring, further wherein an omega-shape of each of the omega-shaped connectors is oriented in the same proximal to distal direction; wherein the stent device has a first configuration in which the plurality of adjacent rings have a first diameter, and the stent device has a second configuration in which the plurality of adjacent rings have a second diameter that is greater than the first diameter, and wherein the flattened tops and the flattened bottoms remain parallel to each other and the shape of the sigmoidal-shaped connectors extends radially as the stent device is expanded from the first configuration to the second configuration.

As mentioned above, the first diameter may be between 0.5 mm and 4 mm and the second diameter may be between 3 mm and 7 mm.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the description are utilized, and the accompanying drawings of which:

In FIG. 1C, the dimensions are in mm.

FIG. 2B shows an end view of the stent device of FIG. 2A with exemplary dimensions (in mm) of the inner and outer un-expanded diameters. FIG. 2C is an "unrolled" configuration of the stent device of FIG. 2A, if the device of FIG. 2A were cut along the longitudinal (e.g. proximal to distal) axis and unrolled to be flat.

FIG. 3B is an end vie of the stent device of FIG. 3A. FIG. 3B is an "unrolled" configuration of the stent device of FIG. 3A, if the device of FIG. 3A were cut along the longitudinal (e.g. proximal to distal) axis and unrolled to be flat.

FIG. 9A shows the exemplary biphasic cell configuration in an un-expanded configuration, while FIGS. 9B and 9C show a progressively more expanded configurations.

FIG. 10A is an example of another variation of a plurality of repeated biphasic shapes (unit cell) including a first open trapezoidal portion having a flattened top side (e.g., a second side) and a proximal-facing opening, and a second open trapezoidal portion having a flattened top side (e.g., a fifth side) forming a distal-facing opening. In this example, the first and second open trapezoidal portions have the same shape (e.g. rounded isosceles trapezoids in which the sides of the trapezoid forming the opening are angled in).

FIG. 10B shows a schematic of an example of a portion of the first open trapezoidal shape having the flattened top, two sides forming the proximal-facing opening, showing the angle ($\alpha'$) formed between a connector region (connecting the first open trapezoidal shape to the second open trapezoidal shape) and the first open trapezoidal shape.

FIG. 15A is an 8×58 mm stent, FIG. 15B is an 8×59 mm stent, and FIG. 15C is an 8×57 mm stent.

FIG. 16A is a 5×38 mm stent and FIG. 16B is a 6×38 mm stent.

FIGS. 18A-18D are tables illustrating properties of different examples of stents as described herein. FIG. 18A shows initial and final lengths and diameters of a 5×18 mm stent graft apparatus. FIG. 18B shows initial and final lengths and diameters of a 5×38 mm stent graft apparatus. FIG. 18C shows initial and final lengths and diameters of a 6×18 mm stent graft apparatus. FIG. 18D shows initial and final lengths and diameters of a 6×38 mm stent graft apparatus.

DETAILED DESCRIPTION

Described herein are stent apparatuses with improved flexibility for greater expansion without fracture. This allows the stents to be expanded to greater diameter sizes when in use, which provides an exemplary benefit of being able to use a single stent for a greater variety of uses (e.g., different vessel sizes) without having to use a differently sized stent. The stents described herein are also adapted such that foreshortening of the stent during expansion is reduced, preventing a variety of complications.

The stents herein generally have a collapsed delivery configuration, and are adapted to be expanded. The "collapsed" configurations may be referred to herein as delivery, collapsed, initial, or other similar term. The delivery configuration can be the configuration the stent has after being manufactured, such as by laser cutting a tubular element or 3-D printing the stent. The stents herein are described as being expanded by balloon expansion, but the stents could be adapted to be able to at least partially self-expand.

Any of the stents herein can include one or more coverings over any portion of the stent.

The stents include a plurality of supports, optionally annular, wherein each of the plurality of supports are connected to at least one adjacent support by one or more connecting portions, which can include one or more connectors.

There are several factors that influence the flexibility of the stents herein and provide the stents with the ability to expand to larger outer dimensions without fracturing. The following are examples of factors that can influence the flexibility of the stents: the configuration of the annular supports and connectors; the dimensions of the annular supports and connectors; and the materials of the annular supports and connectors.

Figure 1A:
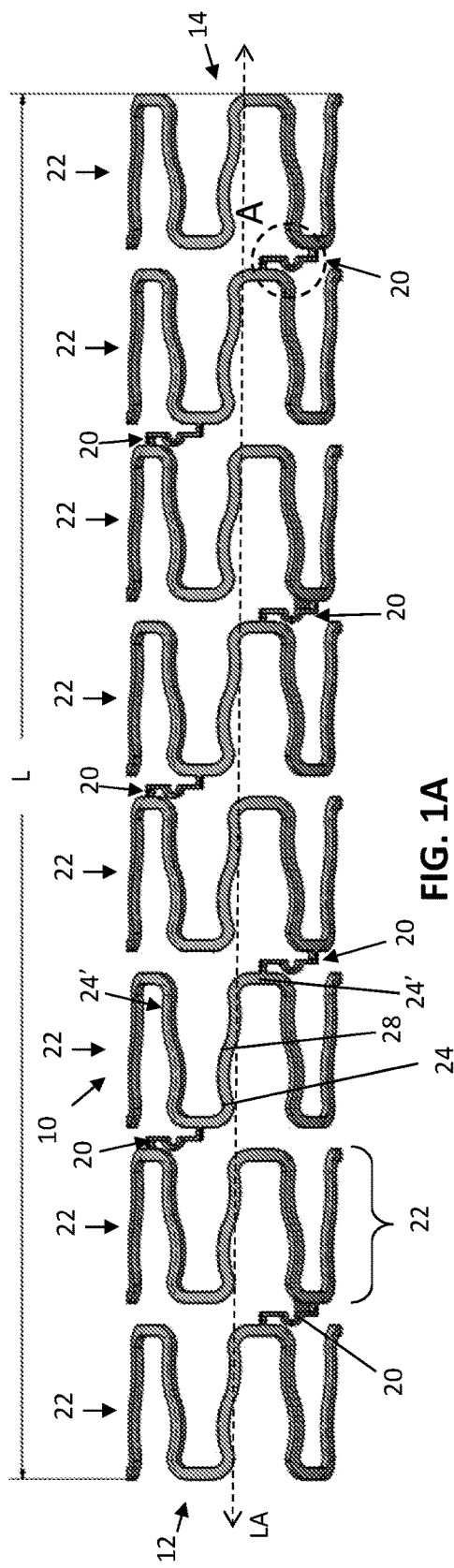
FIG. 1A is a side view illustrating a delivery configuration of an exemplary stent that comprises a plurality of supports coupled together by connecting regions.
Figure 1B:
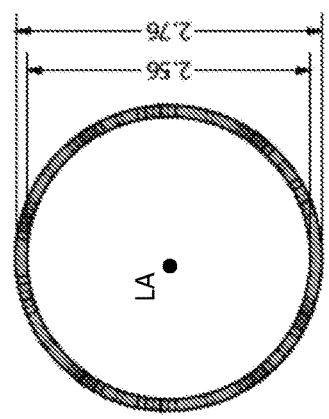
FIG. 1B illustrates an end view of the stent from FIG. 1A.

FIG. 1A illustrates a side view of exemplary stent 10 in an un-expanded (e.g., delivery) configuration, stent 10 having a first end 12 (e.g., proximal end) and a second end 14 (e.g., distal end) and a length, L; thus stent 10 has a longitudinal axis L extending through a lumen defined by the stent. Stent 10 includes a plurality of annular supports 22 ("rings") transverse to the long axis and generally axially spaced from at each other; the individual regions are connected by at least one connector 20 (e.g., omega connector). In this example, an annular support is "adjacent" to another annular support if it is the next annular support when moving towards either the first end 12 or the second end 14. In this example, the annular supports 22 (which may also be referred to herein as "rings") are connected to at least one adjacent support 22 by a connecting portion 20 (omega connector). The rings 22 may be described herein as being "connected" to adjacent rings; it is understand that this may include one or more (e.g., two) omega connectors 20 that may be integrally formed with the rings, such as if the entire stent may be manufactured from a single piece of starting material, e.g., by laser cutting a cylindrical piece.

Each of the rings 22 in this embodiment has a wave configuration, with a plurality of peaks and valleys, repeating in a pattern (only some peaks and valleys are labeled for clarity). In this embodiment, peaks of the supports may extend to the same location along the length of the stent. Valleys of supports (rings) also extend to the same location along the length of the stent. Thus, the peaks (e.g., the flattened top regions 24) may be aligned along the length of the stent device, shown, and the valleys (e.g., the flattened bottom regions 24') may also be aligned along the length of the stent. Peaks and valleys of the waves may define flattened, or squared, ends. Between the peaks and valley are intermediate sections 28 (connecting regions), and in this embodiment the intermediate sections have S-shapes, as can be seen in the side view of FIG. 1A. This embodiment is an example of at least one annular support with a repeating wave pattern having flattened ends connected by curvilinear intermediate sections, such as S-shaped intermediate regions.

In this embodiment, the annular supports all have the same configuration along the length of the stent. Peaks 24 (which are described in additional detail below, and may be referred to herein as a first open trapezoidal portion having a first side, a second side and a third side forming a proximal-facing opening) of adjacent rings may therefore be circumferentially aligned, and valleys (which are described in additional detail below and may be referred to herein as a second open trapezoidal portion having a fourth side, a fifth side and a sixth side) of adjacent rings may be circumferentially aligned.

In alternative embodiments, not every annular support has the same configuration as every other annular support.

Figure 1C:
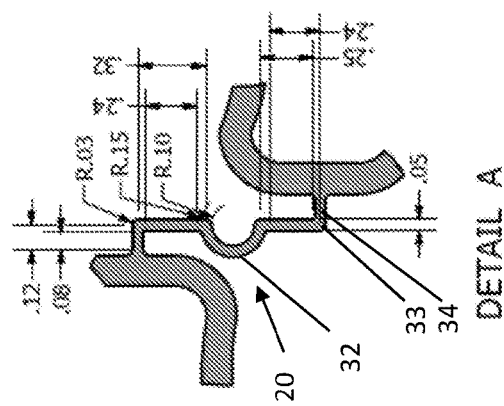
FIG. 1C illustrates a highlighted view of detail of region A shown in FIGS. 1A and 1D. In any of the images and examples provided herein, the dimensions shown are exemplary only, and are intended to provide illustrations of a range of dimensions that may work (e.g., +/− about 50%, 40%, 35%, 30%, 25%, 20%, 15%, 10%, 5%, etc.).
Figure 1D:
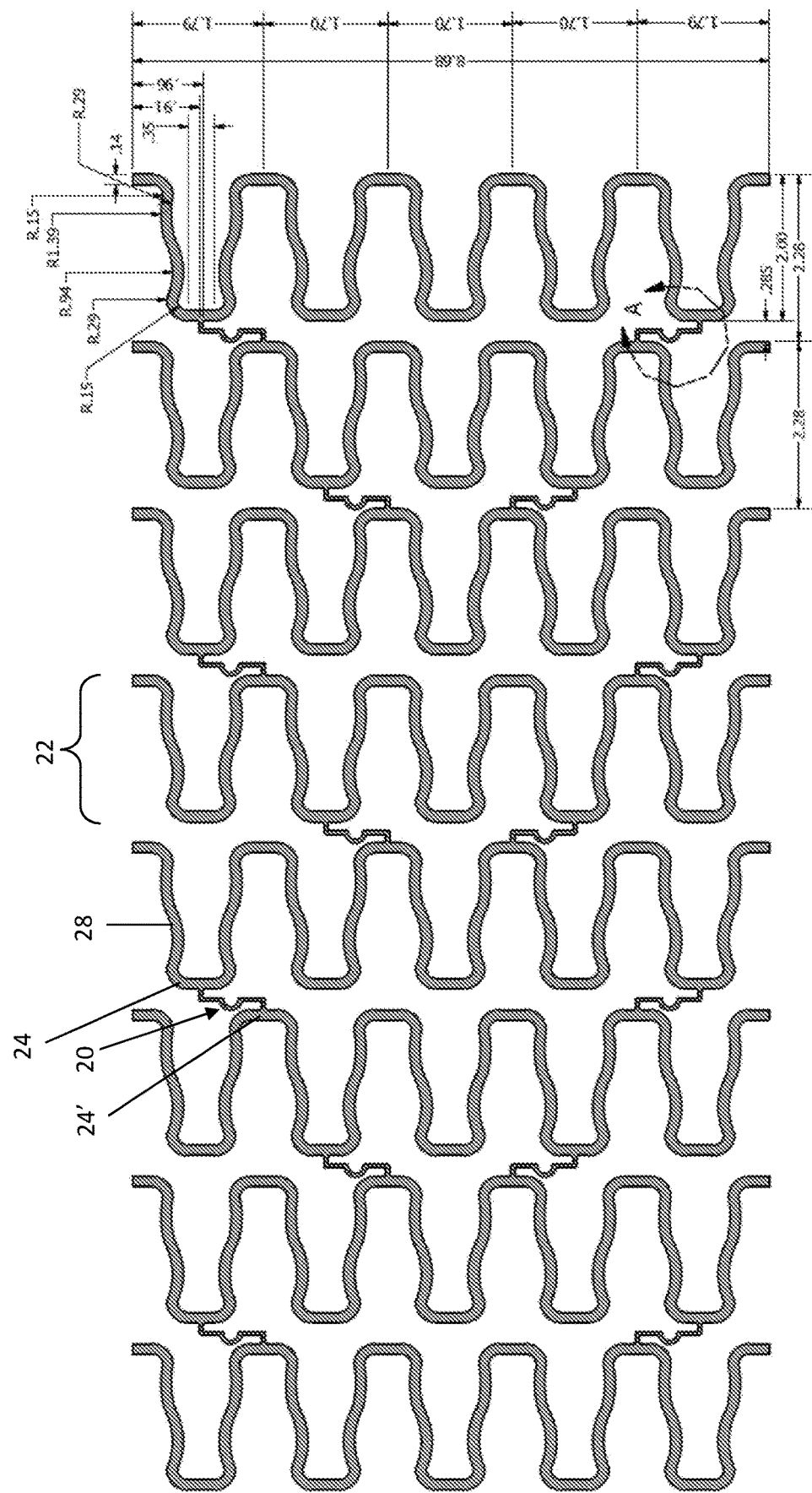
FIG. 1D illustrates the stent from FIG. 1A in a flattened, planar, configuration. Exemplary dimensions (in mm) are shown; as mentioned, the dimensions may be +/− about 50%, 40%, 35%, 30%, 25%, 20%, 15%, 10%, 5%, etc.

Adjacent annular supports 22 are connected together by connecting portion 20. FIG. 1D illustrates a flattened/planar view of an example of a stent device 10, which illustrates the connections between adjacent rings. In this embodiment, the connecting portions 20 (e.g., omega connectors) between adjacent rings 22 include at least two connectors, shown in FIG. 1C as Detail A shown in FIGS. 1A and 1D. FIG. 1C illustrates a connector that connects adjacent rings 22 (only a portion of rings are shown). The connector has a configuration, at least a portion of which has a general "omega" configuration. In this embodiment, the general "omega" configuration is defined by arc region (e.g., dome region) 32 and radial regions 33 generally extending radially outward from arc or domed region 32. In this embodiment, radial regions have linear configurations and may be L-shaped, but in other embodiments they could include some curvature.

The connector (e.g., omega connector) may also include axial regions 34 which may extend generally axially from radial regions 33 and may be parallel to the longitudinal axis LA of the device (e.g., forming the L-shaped ends, mentioned above). Axial regions 33 of the connector are linear but could, in some embodiments, have some curvature to them. One of the axial regions 34 extends further toward first end 12 than the other axial region 34. Radial regions of a connector may generally be aligned when they have linear configurations (and are also aligned with other radial regions of the other connector that connects the two adjacent supports), and axial regions 34 are parallel to each other, and to the longitudinal axis LA.

The "omega" shape is generally defined by an arc or domed region 32 and radial regions 33. While domed region 32 and radial regions 33 do not form an exact, traditional, "omega" Greek letter, it is understood that they form a general "omega" shape of the connector. Domed regions 32 and radial sections 36 can have slightly varying configurations and that portion of the connector can still have a general "omega" configuration as that term is used herein.

The connector extends from a flattened top region (e.g., of the open trapezoidal 'peak' region 24) of a first ring 22 to a flattened top (e.g., of the next open trapezoidal 'valley' region 24') of an adjacent ring 22, as can be seen in FIGS. 1A and 1D. The first open trapezoidal portion (e.g., peak) and second open trapezoidal portion (valley) from which the connector extends are not circumferential aligned. For example, a connector extends from a first open trapezoidal portion 24 on a first ring 22 to a second open trapezoidal portion 24' on an adjacent ring, as shown in FIGS. 1A, 1C and 1D.

As can be seen in FIG. 1D, the arc regions of all of the omega-shaped connectors have similar configurations, and are all oriented in the same direction. In this embodiment, each pair of adjacent supports is coupled together by two omega-shaped connectors, each of which has the configuration shown in FIG. 1C. As can be seen in FIG. 1D, the omega-shaped connectors in any given connecting portion are not circumferentially aligned with the connectors in the adjacent connecting portion, but they are circumferentially aligned with the connectors in the next adjacent connecting portion. In this embodiment, the position of the omega connectors are in an A-B-A-B pattern, with every-other ring having connectors that are circumferentially aligned.

The first and second open trapezoidal potions of the repeating biphasic shapes forming each ring are connected by an intermediate section (e.g., connecting the peak and a valley regions) as described above. In FIG. 1D, the connecting intermediate section is a length that extends in an angle between the open trapezoidal portions; this connection may be straight or curved (e.g., sinusoidal, including s-shaped). As will be described in greater detail below, this intermediate section, and in some variations the 'legs' of the open trapezoidal portions (forming the openings) may change their angle relative to the flattened top region when the stent devices expand (e.g., when driven by a balloon to expand).

In FIG. 1D the two omega-shaped connectors 20 extend from adjacent peaks 24' and 20, on an adjacent rings. In this embodiment the two connectors extend from adjacent flattened top (or bottom) regions. In the example shown in FIGS. 1A-1D, there are three flattened top regions (peaks) between some of the omega-shaped connectors (from which no connector extends), and on flattened top region (peak) on the other side (radially) between the two omega-shaped connectors. Thus, in the space between each set of rings, two omega-shaped connectors are connect the adjacent rings, and this connecting pattern is offset and alternating with every other ring, as shown in FIGS. 1A-1D.

In some variations, only three or fewer (e.g., two) connectors are used to connect adjacent rings. For example, by having only two connectors in each connecting region, there is less area of material than in some other stent designs. This smaller area may allow the stent to have more flexibility and can expand to a greater extent when forces are applied on the stent such as by an expansion balloon. In alternative embodiments, however, there could be more than two connectors in a connecting portion, and the desired flexibility could still be maintained by modifying one or more other aspects, such as, for example without limitation, one or more dimensions (e.g., thickness, radius), configuration, or material.

In general, each ring may be formed of a length of material, such as a metal (e.g., a nickel titanium alloy, a chromium alloy, a stainless steel alloy, etc.). The length of material may be a strip of material formed into a rectangular or square cross-section (e.g., which may be formed by laser cutting from a tube of the material), or in some variation it may be formed of a wire.

The dimensions of the rings are one factor that may influence the flexibility and may provide for greater expansion of the stents herein. Less area of the stent material generally increases the flexibility and allows the stent to expand to greater outer dimensions without fracture. FIG. 1D shows exemplary dimensions and radii for portions of at least one of the rings. In some embodiments the thickness of the support material is from 0.08 mm to 2.0 mm, such as from 0.1 mm to 1.8 mm, such as from 1.2 mm to 1.6 mm (e.g., 1.2 mm, 1.3 mm, 1.4 mm, 1.5 mm, 1.6 mm).

The configuration of the ring, including the arrangement of the repeating biphasic cells (e.g., the first and second open trapezoidal portions) of the rings is another factor that influences the flexibility and provides for greater expansion of the stents herein. The plurality of adjacent rings (e.g., annular supports) 22 generally have a wave-like configuration, with squared (flattened) end and S-shaped intermediate sections in between these flattened ends (forming peaks and valleys). As shown in the exemplary FIG. 1D, the connecting regions 28 between the open trapezoidal portions (or more specifically, between the flattened tops) are not aligned with the longitudinal axis of the stent. That is, they are at an angle relative to the longitudinal axis. This angle can increase the flexibility of the stent and allow for greater expansion.

As mentioned above, the dimensions of the omega-shaped connectors are an additional factor influences the flexibility and provides for greater expansion of the stents herein. FIG. 1C shows exemplary dimensions (e.g., thicknesses and radii) that can be used for any of the omega-shaped connectors herein. In some embodiments, one or more omega-shaped connectors have a thickness from about 0.02 mm to about 1 mm, such as about 0.02 mm to about 0.8 mm (e.g., about 0.02 mm about 0.03 mm, about 0.04 mm, about 0.05 mm, about 0.06 mm, about 0.07 mm, about 0.08 mm, etc.).

The configuration and number of the omega-shaped connectors are other factors that influence the flexibility and provides for greater expansion of the stents herein. As set forth herein, at least a portion of the omega-shaped connectors may have a general omega configuration, including an arc (e.g., domed) section. The omega configuration provides for added flexibility in the connecting portions. Additionally, in some embodiments the connecting portions only include two omega-shaped connectors, which reduces the area of the connecting portions and increases the flexibility.

Figure 1E:
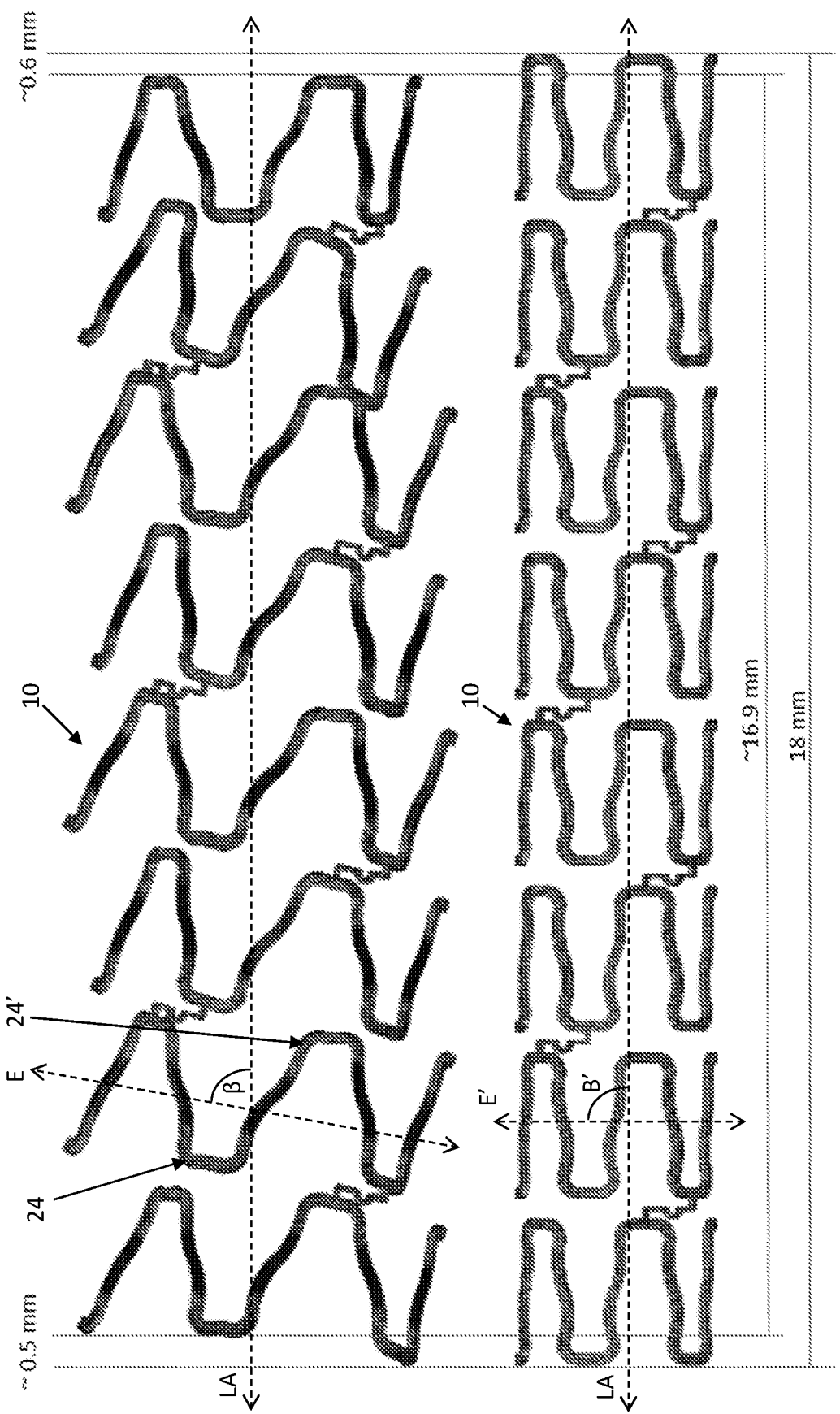
FIG. 1E illustrates the stent from FIG. 1A in an initial (unexpanded, bottom) configuration and an expanded (top) configuration. Shading indicates relative strain on the frame of the stent shown.

FIG. 1E illustrates an expanded configuration (top) of the stent 10 from FIGS. 1A-1D. The bottom configuration in FIG. 1E is the same stent device 10 as shown in FIG. 1A. The top in FIG. 1E illustrates the stent 10 (which has an initial, unexpanded outer diameter of approximately 2.76 mm-see FIG. 1B) expanded to an outer diameter of about 8 mm, about 2.9 times the initial outer dimension. FIG. 1E also illustrates the foreshortening that the stent undergoes as it is expanded. The initial length is 18 mm, and the length when expanded is about 16.9 mm, shortening by about 1.1 mm. In this embodiment the stent foreshortened by not more than about 6.2% when expanded to about 2.9 times an initial outer diameter. The ability to expand this much with so little foreshortening is due in part to the configuration of the rings and omega-shaped connectors, the dimensions of the rings and omega-shaped connectors, and the material(s) forming the stent.

As can also be seen in the top view of FIG. 1E, when the stent is expanded, the flattened top of the first open trapezoidal portion (peak) 24 is rotated along the radius of the stent, e.g., away from the longitudinal axis of the stent, with the flattened tops (or bottoms) of the next open trapezoidal portion (valley) 24' also rotated, but still parallel with the first flattened top 24. The plane of each ring is shown rotated by angle (β) relative to the long axis (LA) compared to the initial configuration shown in the bottom of FIG. 1E, showing the unexpanded configuration. The flatten tops of peaks 24 and may be individually flared radially outward relative to the flattened tops of the valleys 24' when the device is expanded. The angle of rotation can be anywhere from 5 degrees to 60 degrees, such as from 10 to 45 degrees.

As is also shown in the bottom of FIG. 1E, each ring may have an axis or plane E' that is orthogonal to the longitudinal axis (LA). When the stent is expanded, in this example the annular supports (rings) expand in such a manner than the axis rotates with respect to the longitudinal axis, and as shown in the expanded top configuration, the plane of the rings has rotated relative to the longitudinal axis. The angle β is less than 90 degrees (compared with the original angle of β' which is approximately 90 degrees in this example).

Figure 1F:
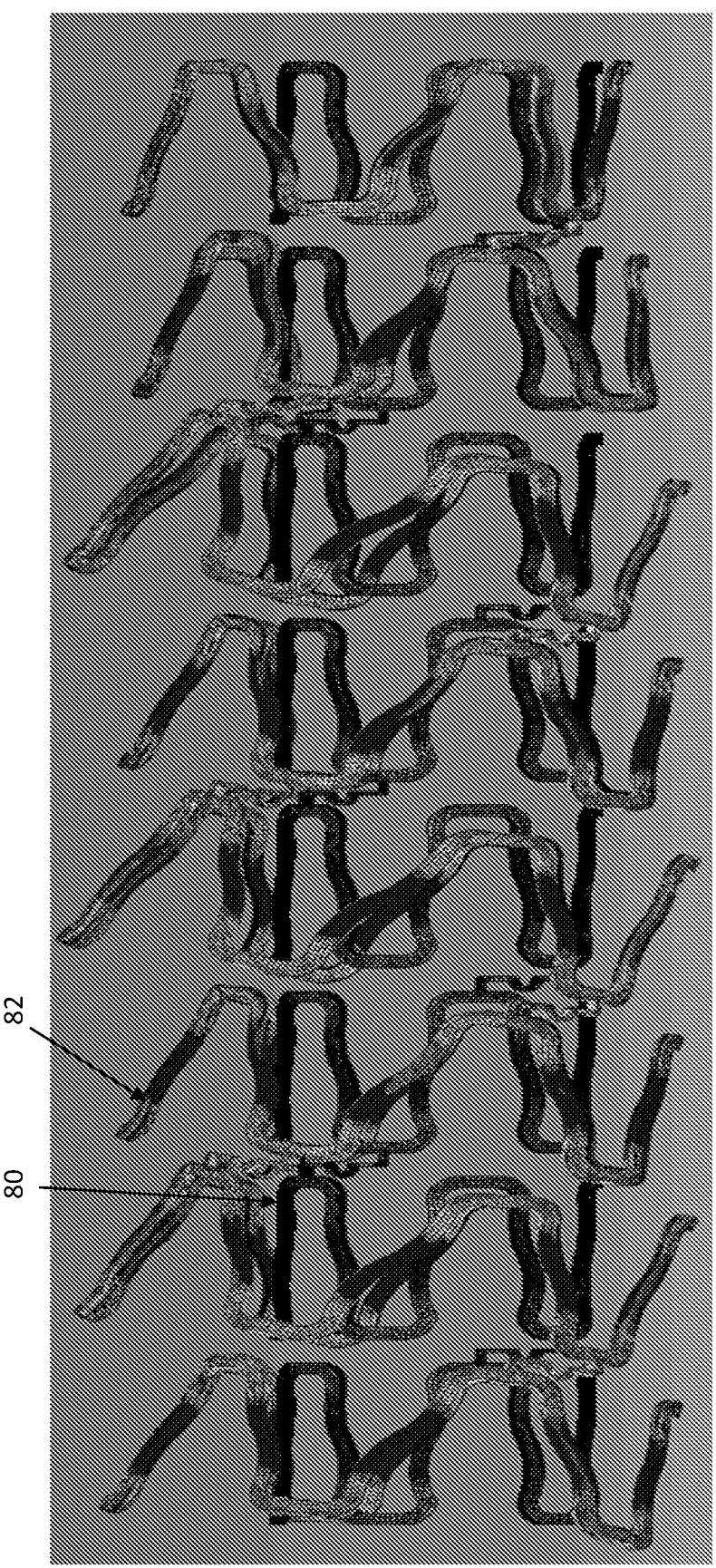
FIG. 1F overlays the two configurations shown side-by-side in FIG. 1E.

FIG. 1F illustrates the initial 80 and expanded 82 configurations from FIG. 1E overlaid on top of each other, which can further highlight the disclosure described with respect to FIG. 1E.

It is understood that not every features show in the embodiments herein is necessary to increase the flexibility of the stents herein. For example, in alternative embodiments, some connecting portions can have three connectors, and the stent may still be able to expand to desired outer dimensions for some applications.

As set forth above, one of the exemplary advantages of stents herein is that they can be mounted on different diameter expansion balloons and can be expanded to a greater variety of outer dimensions. This can reduce the number of stents that must be available for use for a particular medical application.

Figure 2B:
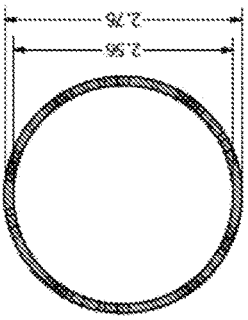
FIGS. 2A-2C illustrate view of an exemplary stent similar to the exemplary stent shown in FIGS. 1A-1F. A side view of the stent is shown in FIG. 2A.
Figure 2A:
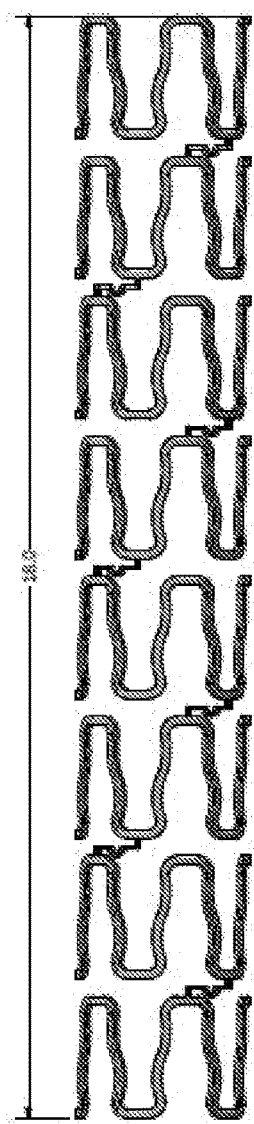
Figure 2C:
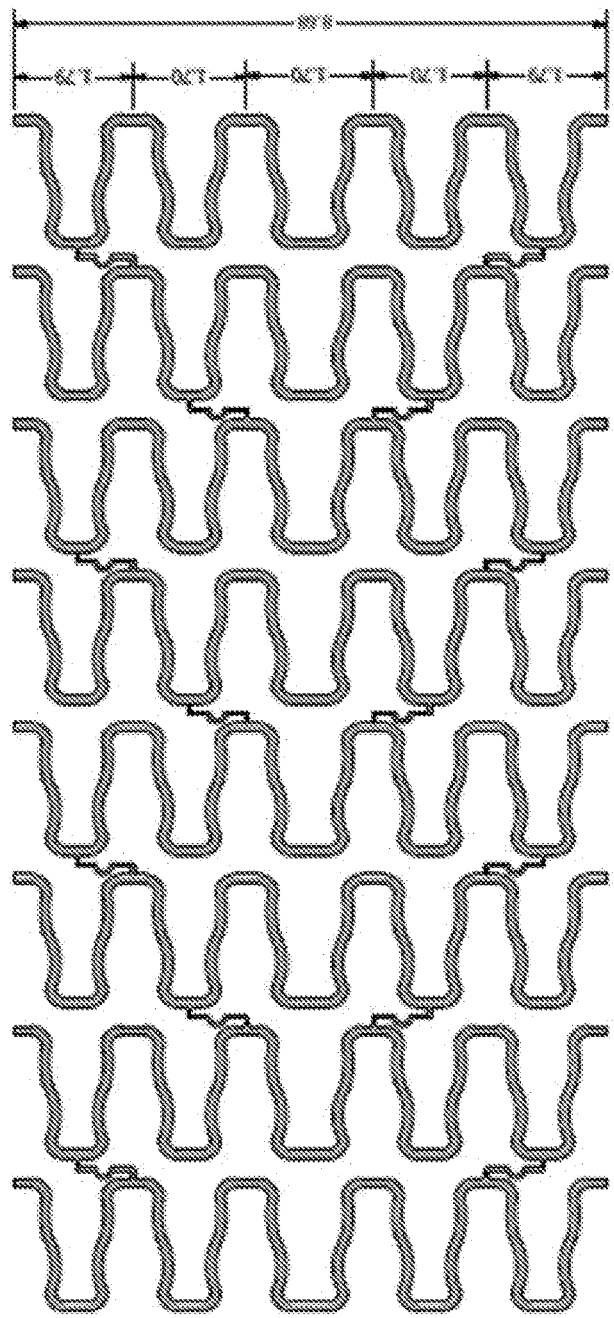

FIGS. 2A-2C illustrate an exemplary stent that is similar in many ways to the exemplary stent in FIGS. 1A-1E. The general configurations of the annular supports and connectors is the same to those in FIGS. 1A-1E. One difference is that the initial outer dimension of the stent is shown as 2.83 mm (see, e.g., FIG. 2B), as opposed to 2.76 mm in the embodiment in FIG. 1A-1E. The initial larger outer dimension allows the stent in this embodiment to be expanded to larger outer dimensions without fracturing. Another difference is the distance between peaks in one circumferential region of the stent. As shown in FIG. 2C, one distance between the peaks in the center of the stent is 1.90 mm, whereas in FIG. 1A-1E it was 1.70 mm (see FIG. 1D). Any of the other features described with respect to the embodiment in FIGS. 1A-1E can be incorporated in this embodiment as well.

Figure 3A:
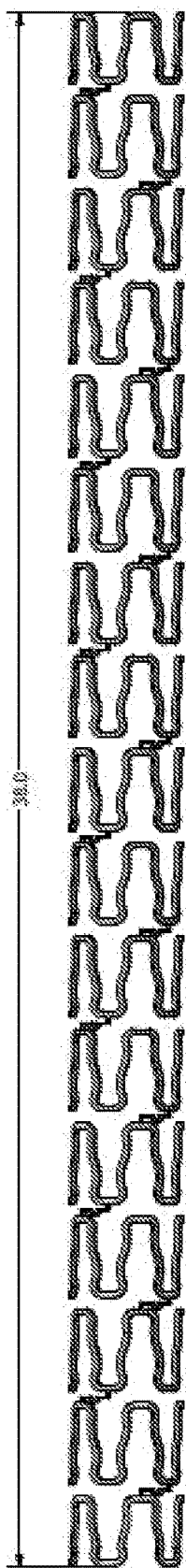
FIGS. 3A-3C illustrate view of an exemplary stent similar to the exemplary stent shown in FIGS. 1A-1F and 2A-2C. A side view of the stent device is shown in FIG. 3A.
Figure 3B:
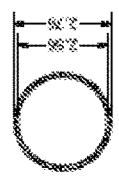
Figure 3C:
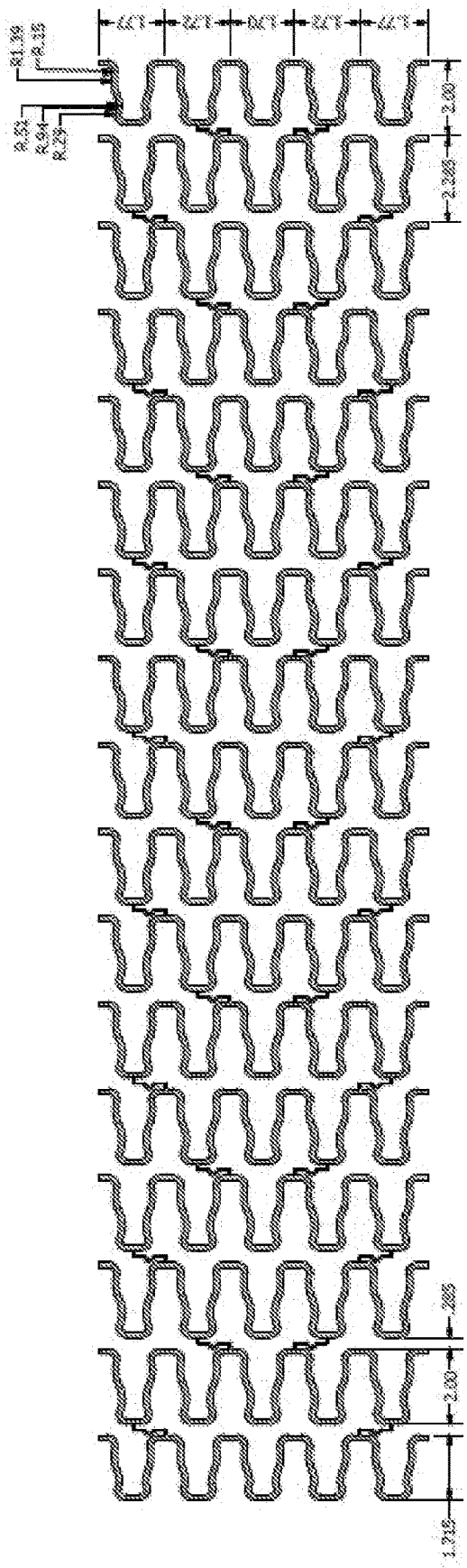

FIGS. 3A-3C illustrate an exemplary stent that is similar in many ways to the exemplary stent in FIGS. 1A-1E and 2A-2C, and any feature therein can be incorporated into this embodiment as well. This embodiment is longer than the embodiments in FIGS. 1A-1E and 2A-2C, with the exemplary length of 38 mm. The outer dimension of 2.76 mm shown in FIG. 3D is the same as in the embodiment in FIG. 1A-1E. The distance between adjacent peaks is slightly different than the embodiments in FIGS. 1A-1E and 2A-C, as shown in FIG. 3C. The connectors can have any of the dimensions of any of the connectors herein. Other exemplar dimensions are also provided in FIG. 3C.

The stents can generally be any appropriate length and have any appropriate initial outer dimension.

Exemplary materials for any of the stents herein include cobalt-chrome alloys (e.g., L605) y 316 L stainless steel. Expandable polytetrafluoroethylene (ePTFE) and polyester (PET, dracon) are examples of materials that can be used for one or more sleeves, coatings or coverings on the stent, if included.

Figure 4A:
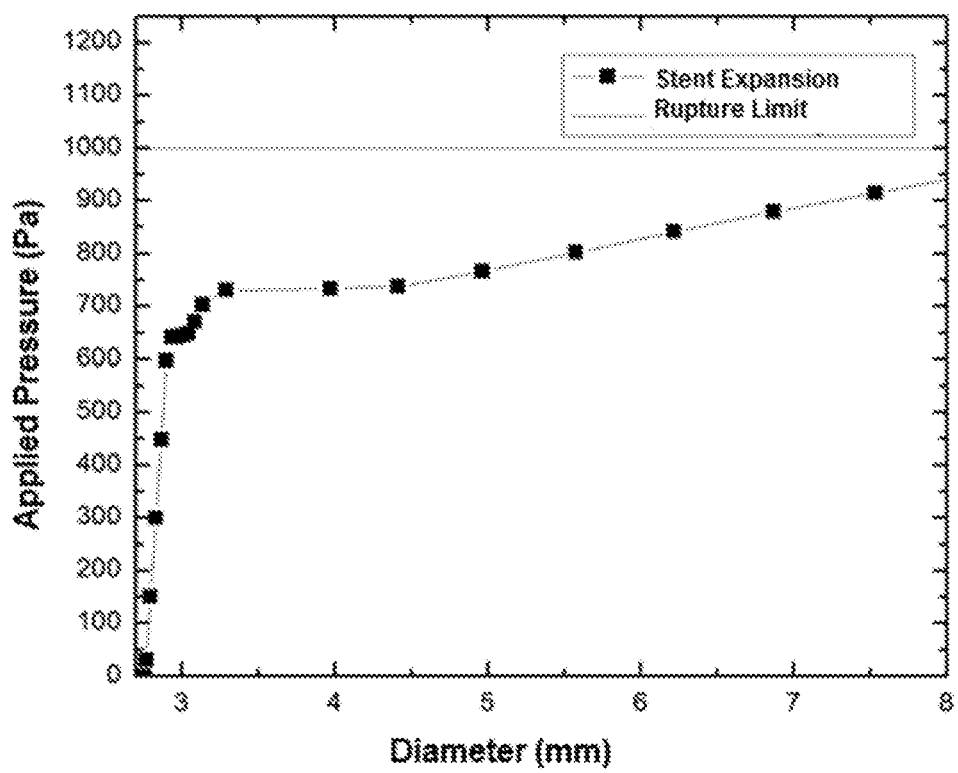
FIG. 4A is a graph illustrating an example of an applied pressure vs. diameter profile of one example of a stent apparatus as described herein.
Figure 4B:
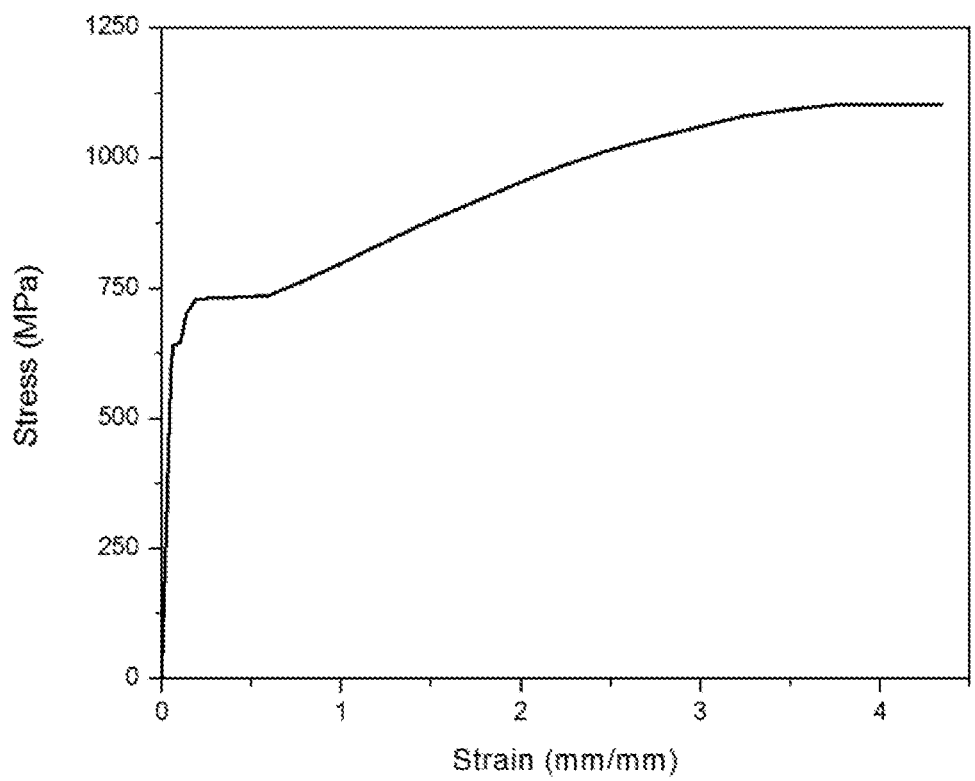
FIG. 4B is a graph illustrating an example of a stress-strain profile of one example of a stent apparatus as described herein.

FIG. 4A illustrates a pressure versus diameter graph for the stent shown in FIGS. 1A-1E, illustrating a pressure applied by an internal expansion balloon. When plotting applied pressure vs corresponding outer diameter values, stent expansion progresses gradually until reaching approximately 7.5 bar pressure. From this pressure, more accelerated expansion starts, being more susceptible to expansion as pressure increases, until reaching about 8 mm, a maximum expansion value. It is noted that this exemplary stent is configured to be able increase its diameter in approximately 2.9 times without showing fracture hazard. When removing applied pressure, a slight stent recovery occurs due to initial elastic deforming. Similarly, FIG. 4B shows an example of a stress vs. strain curve for a stent device such as those shown in FIGS. 1A-1F, 2A-2C and 3A-3C. In this example, the stress (in MPa) vs. strain (mm/mm) follows a similar profile to that shown in FIG. 4A for applied pressure vs. diameter over the ranges examined.

Figure 5:
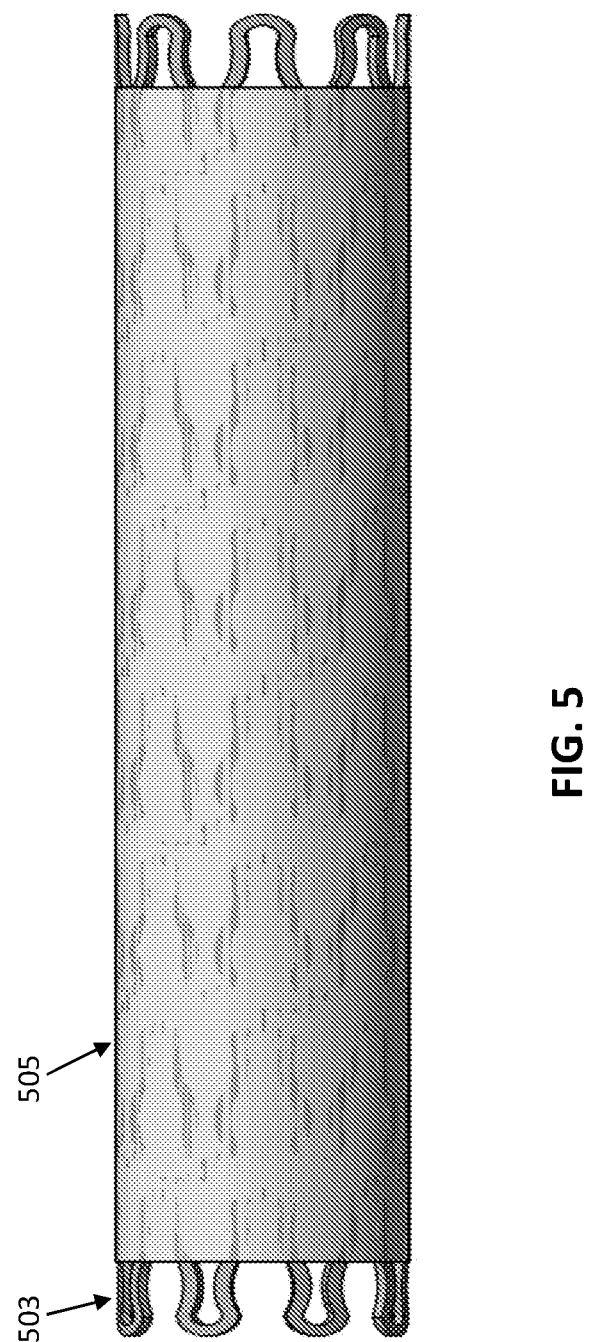
FIG. 5 illustrates an exemplary stent device including an optional sleeve (covering).

As mentioned, any of the stent devices descried herein may include a sleeve, cover, coating or the like. For example, FIG. 5 illustrates an exemplary stent device (which can be any of the stents described herein), at least a portion of which is covered by a sleeve 505. In this example, the ends of the stent frame 503 are uncovered by the sleeve. Examples of sleeves that may be used are described in greater detail below.

Figure 6:
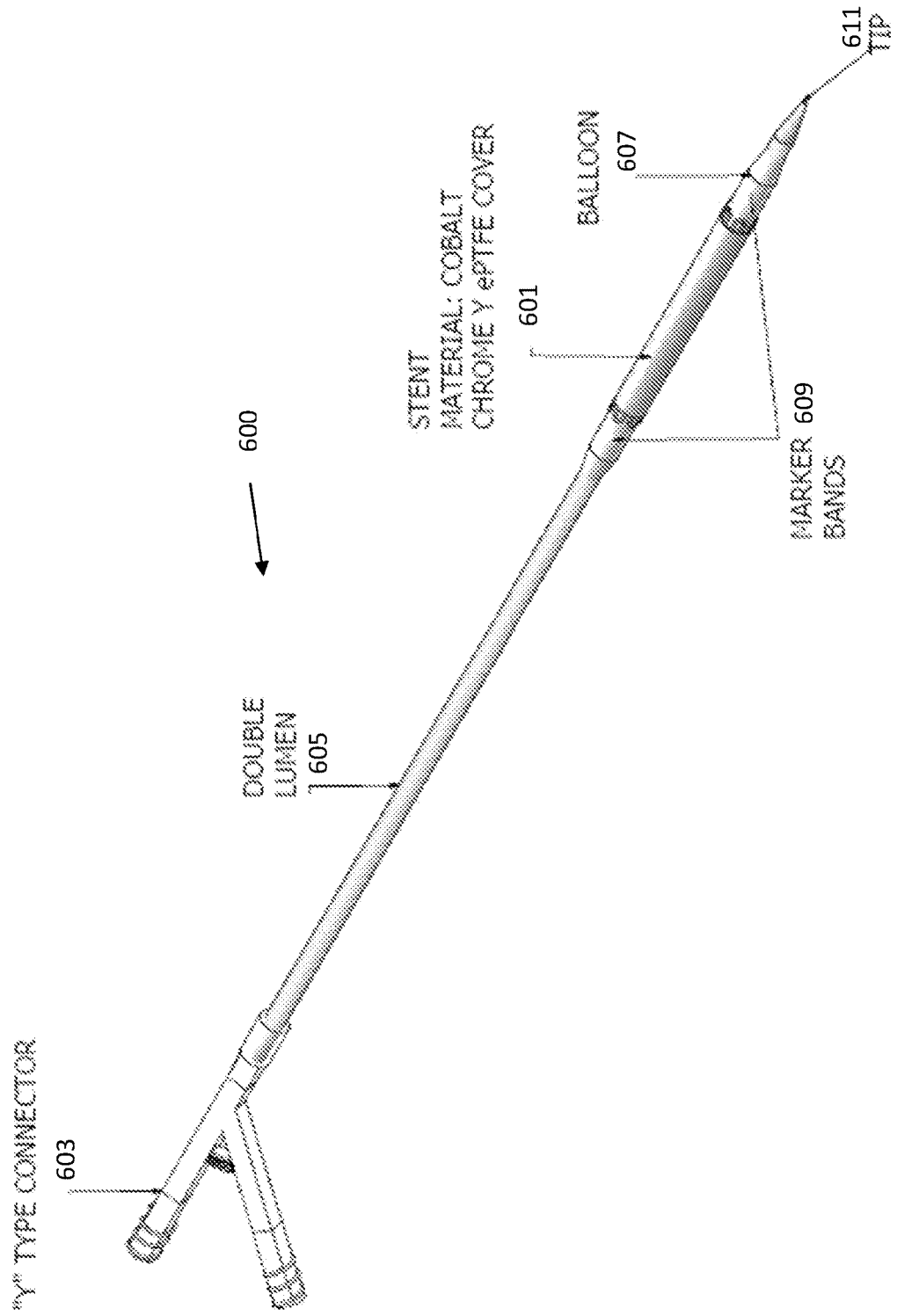
FIG. 6 illustrates an exemplary catheter system for delivering any of the stents devices herein. Any of these stent devices may be included with all or some of the delivery components shown in FIG. 6.

FIG. 6 is a perspective view illustrating an exemplary catheter system 600 for delivering any of the stents 601 described herein. This system may include a connector 603 connected to an elongate lumen 605 for inserting the stent device 601 over an expandable balloon 607. The balloon may be inflated by applying fluid through the catheter (e.g., one of the lumen of the catheter 605). One or more imaging markers 609 may be included to aid in visualizing the stent when in the body, e.g., using fluoroscopy. The tip 611 of the device may be open and a lumen through the device may be used for advancement over a guidewire (not shown).

The devices described herein may be used anywhere appropriate in the body, including, but not limited to, the peripheral vasculature. For example, a merely exemplary location for placement of the stents herein can be in tibial arteries, such as for injury to such arteries. The primitive iliac artery has a diameter between about 5 and 8 mm, and may be well suited for stents herein.

EXAMPLES

Figure 7:
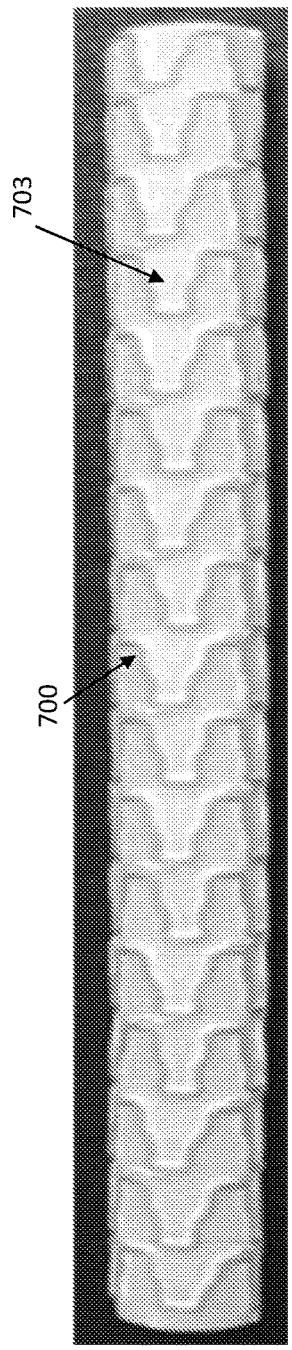
FIG. 7 shows an example of an apparatus as described herein, configured as a balloon-expandable chrome cobalt stent, including plurality of adjacent rings connected together by 3 or fewer omega-shaped connectors (e.g., two connectors) between adjacent rings. The stent device in FIG. 7 shows a lateral view.

FIG. 7 shows another example of a stent 700 as described herein. The stent may include a sheath or cover 703. For example the stent device frame, formed of a plurality of interconnected rings, as described above, may be embedded in a polymeric matrix 703, such as Bioweb® (Zeus Industrial Products Inc). The layers of this polymeric matrix may be applied, e.g., by electrospinning to the entire structure of the stent frame, providing a great deal of flexibility and structural stability. This may also improve its radial proprieties and allow the vascular vessel to open and recover the blood flow.

Figure 13:
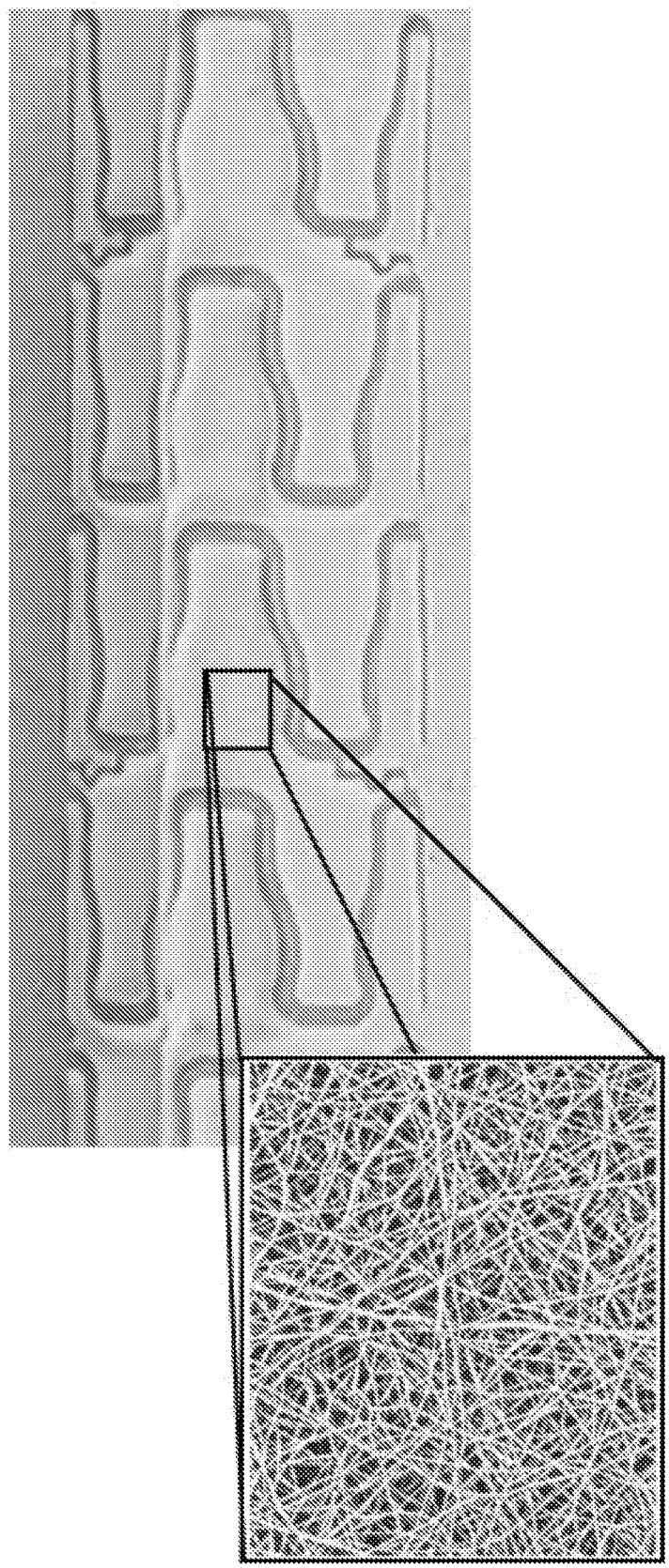
FIG. 13 is an example of a stent apparatus as described herein including a cover having a pores encapsulating the metallic frame of the stent as described herein.

FIG. 13 illustrates one example of a sleeve encapsulating a stent frame. In this example, the sleeve is formed of a porous material (such as ePTFE) that is applied to the frame in an average thickness of between, e.g., about 0.001 inches to about 0.010 inches (e.g., between about 25 micrometers to about 250 micrometers, between about 40 to about 80 micrometers, between about 50 to about 70 micrometers, etc.). The pores may be a variety of different sizes, depending upon the needs. In some variations the sleeve may be formed by electrospinning the material onto the stent frame, using polymer fibers with thicknesses ranging from nanoscale to microscale. Fabrics with complex shapes can be electrospun from solutions, producing a broad range of fiber and fabric properties. This technique has the ability to create encapsulation technology, spin membrane/sheet, and develop 3-D structures for coating substrates of varying shapes and sizes.

Figure 8C:
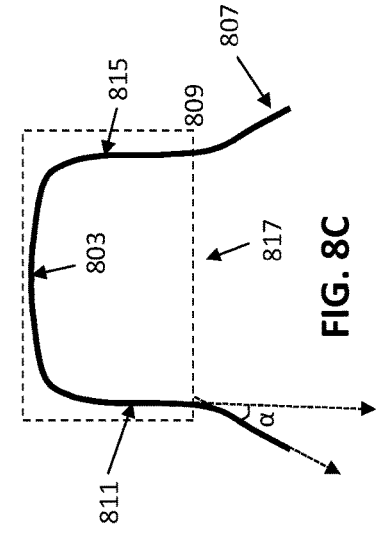
FIG. 8C shows a schematic of an example of a portion of the first open trapezoidal shape having the flattened top, two sides forming the proximal-facing opening, showing the angle formed between a connector region (connecting the first open trapezoidal shape to the second open trapezoidal shape) and the first open trapezoidal shape.
Figure 8B:
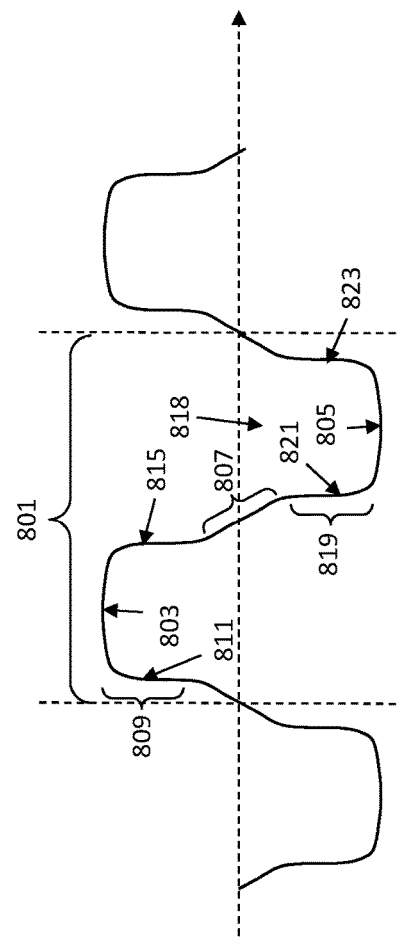
FIG. 8B shows a schematic of a plurality of repeated biphasic shapes (unit cell) including a first open trapezoidal portion having a flattened top side (e.g., a second side) and a proximal-facing opening, and a second open trapezoidal portion having a flattened top side (e.g., a fifth side) forming a distal-facing opening.

Returning to FIGS. 8A-8C, in general, the rings are formed of a length of material (e.g., metallic and or polymeric material) that forms, around the radius of the stent, a pattern of repeating biphasic cells, as shown in FIG. 8B. The repeating biphasic cells 801 typically include a pair of flattened top regions 803, 805 that are connected by an intermediate region 807. In some variations the flattened top region forms a pair of open trapezoidal portions, such as shown in FIG. 8C. In FIG. 8C, the open trapezoidal portion (dashed box 809) includes a first side or leg 811, a second side (corresponding to the flattened top 803), and a third side or leg 815. This open trapezoidal portion has a distal-facing opening 817. Similarly, a second open trapezoidal portion 819, oriented 180 degrees off of the first open trapezoidal portion 809, includes a fourth side 821, a fifth side (corresponding to the flattened top 805), and a sixth side or leg 823. The second open trapezoidal portion has a proximal-facing opening 818. The first and second open trapezoidal portions may be connected by intermediate regions 807. For example, the third side 815 of the first open trapezoidal portion may be connected to the fourth side of the second open trapezoid portion by a connector region 807, as shown, and the first side of the first open trapezoidal portion is connected to the sixth side of a second open trapezoidal portion of the next biphasic cell.

Figure 9A:
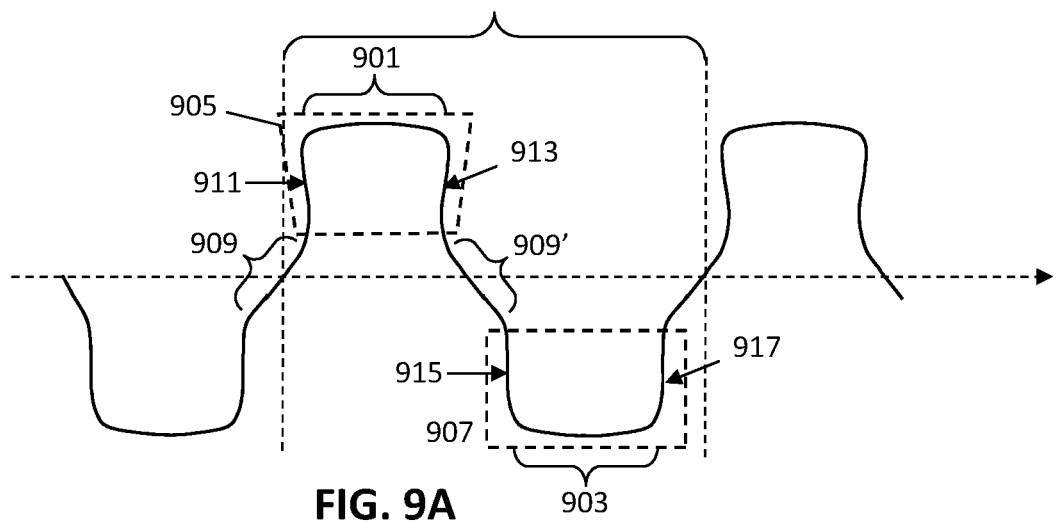
FIG. 9A-9C illustrate expansion of another example of a portion of a ring of a stent device including a repeating pattern of biphasic cells, each biphasic cell comprising a first open trapezoidal portion having a first side, a second side and a third side forming a proximal-facing opening, and a second open trapezoidal portion having a fourth side, a fifth side and a sixth side forming a distal-facing opening, in which the first open trapezoidal portion is connected to the second open trapezoidal portion.
Figure 9B:
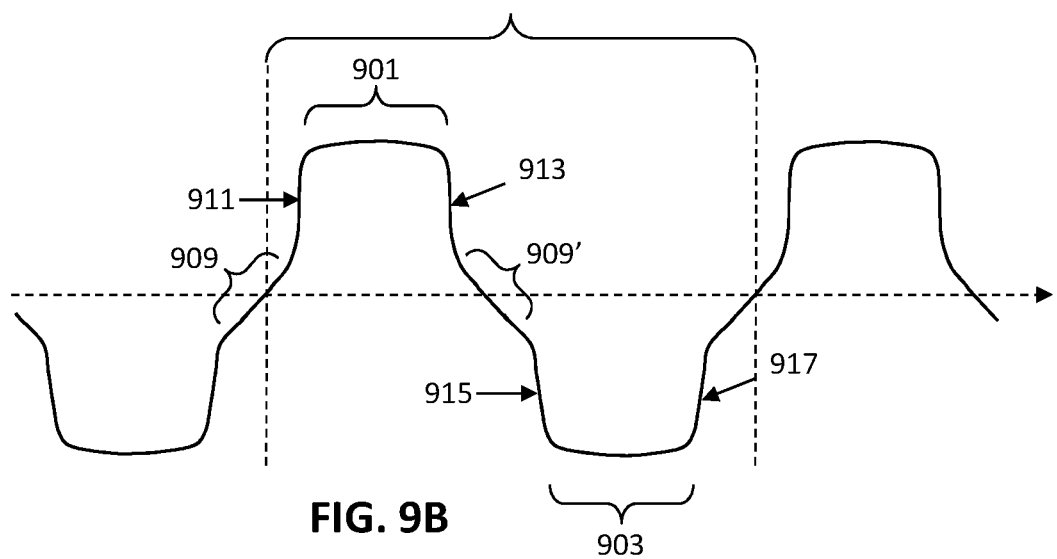
Figure 9C:
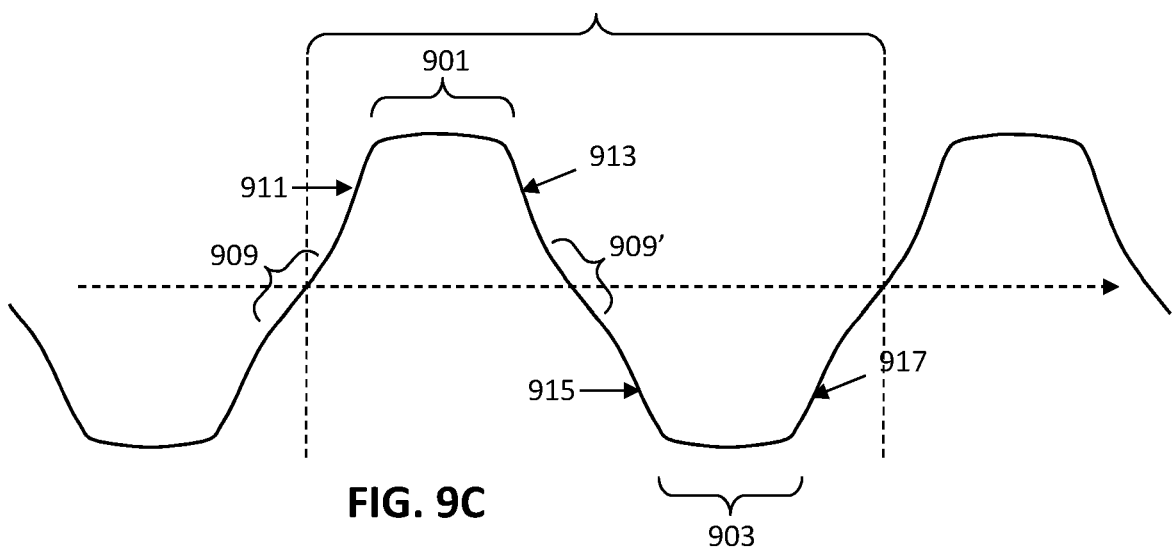

The first open trapezoidal portion and the second open trapezoidal portion may have different 'trapezoidal' shapes. For example, in FIG. 8B, the first and second open trapezoidal shape is approximately rectangular 809, and open on one side, as shown in FIG. 8C. Both the first and second open trapezoidal portions in the exemplary biphasic cell shown in FIG. 8C are the same general shape. FIGS. 9A-9C illustrate another example of a repeating biphasic cell forming a ring of a stent device as described herein, in which the first biphasic cell is an open trapezoidal portion having an isosceles (or keystone) shape 905, while the second open trapezoidal portion 907 has a more rectangular shape, at least in the un-expanded shape (shown in FIG. 9A). The dimensions of the open trapezoidal portions (e.g., the lengths of the flattened top regions 901, 903) are approximately the same.

FIGS. 10A-10B illustrate another example of a repeating biphasic cell 1001 in with the first and second open trapezoidal portions 1005, 1007 are approximately the same (e.g., isosceles) shape. As shown in FIG. 10B, the open trapezoidal portion 1005 in this example includes first 1009, second (flattened top 1011) and third 1013 sides. The first 1009 and third 1013 sides are angled inwards forming the open isosceles trapezoidal shape. The angle ($\alpha$) shown provides and angle of the first or third sides relative to the intermediate connector 1017.

As shown in all of these examples the open trapezoidal shapes may have rounded (curved) edges. In some variations the open trapezoidal shapes may have straight edges (e.g., angled edges). In addition, the flattened tops (e.g., 803, 805, 901, 903) may be flat or approximately flat, as shown. Thus, they may be curved slightly (typically <15 degrees of curvature, e.g., <12 degrees, <10 degrees, <8 degrees, etc.). The flattened tops of the first and second open trapezoidal portions shown are parallel, where in the context of the flattened (e.g., slightly curved) tops, the term parallel means substantially, parallel, so that an average vector through the flattened top portion of the first open trapezoidal portion (see, e.g., 832, FIG. 8A) is parallel to an average vector through the flattened top portion of the second open trapezoidal portion.

Figure 8A:
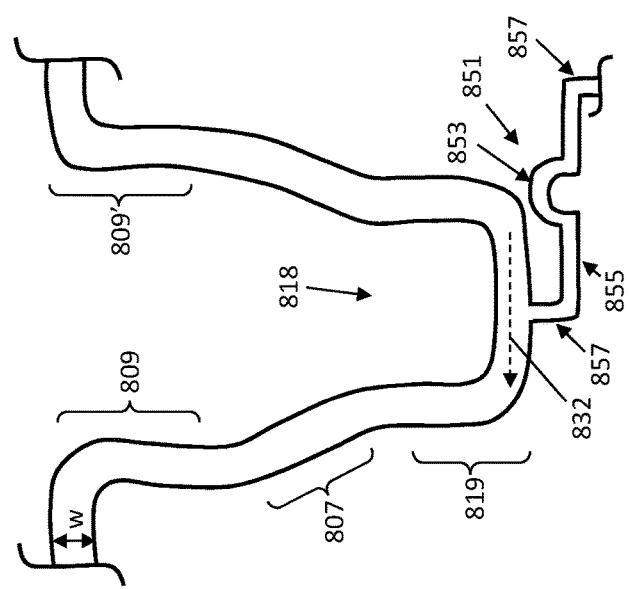
FIG. 8A is an example of a portion of a stent apparatus, showing an open trapezoidal region including a flattened surface to which an omega-shaped connector is attached.

FIGS. 8B-8C, 9A-9C and 10A-10B schematically illustrate the repeating biphasic cells; in practice the cells may be formed of a length of material having a width, w, as shown in FIG. 8A. In this example, the width is constant; in some variations the width may be narrower, e.g., in the intermediate region connecting the open trapezoidal regions. In FIG. 8A, the exemplary portion of the repeating biphasic cell shows an open trapezoidal portion 819 having a proximal-facing opening 818 and half of the adjacent open trapezoidal portions 809, 819' having distal-facing openings. FIG. 8A also shows an example of an omega-shaped connector 851 that is connecting to the flattened top of the open trapezoidal portion 819 at a middle region. The omega connector includes an arc ("domed") region 853 and two laterally extending arms extending from the arc 855. The ends of the omega-shaped connectors may be L-shaped 857, 857' so as to connect perpendicularly to the flattened top(s).

In general, the repeating biphasic cells forming the rings may have a generally interconnected "U" shape, with the U-shapes alternating as distal-facing and proximal facing radially around the circumference of the stent in each ring. As shown and described above, the generally U-shaped geometry may also be described an open trapezoidal portion. Thus, the U-shapes may have an inwards curved part in the beginning of the figure and afterwards an outwards curve. The tops of the U's may be connected to each other by an intermediate region, which may be angled or curved, as shown. Thus, the repeating biphasic cell may be formed of a pair of connected U-shapes.

The repeating biphasic cell shapes allow the stent to expand adequately and give the stent enough stability to expand and maintain the peripheral vascular vessel open. The radial stability and homogeneity of the stent may be improved by including a sheath, e.g., embedding it in a membrane, as described above.

FIGS. 9A-9C illustrate the effect of expansion of the stent on a portion of a ring, showing the movement of the intermediate region 909 and/or the legs of the open trapezoidal region(s) as the device transitions from an unexpanded configuration (shown in FIG. 9A) to an expanded configuration (shown in FIG. 9C). For example, in FIG. 9A the repeating biphasic cell pattern is shown in the unexpanded configuration, and the first and second open trapezoidal portions 905, 907 are shown with the first 911 and third 913 sides and fourth 915 and sixth 917 sides angled slightly inwards and the first and second open trapezoidal portions 905, 907 are connected to each other by an intermediate region 909 (adjacent repeating biphasic cells are also connected by intermediate regions 909'). FIG. 9B shows a schematic of the repeating biphasic cell of FIG. 9A after the ring formed by the repeating biphasic cell has begun to expand, e.g., by applying an expansion force from a balloon. In FIG. 9B, the first and third sides of the proximal-facing open trapezoidal portion 901 have opened slightly (e.g., expanding the open trapezoidal shape) and the angle of the intermediate regions 909, 909' has changed as well. Similarly, the fourth 915 and sixth 917 sides have also opened slightly. As expansion continues, in FIG. 9C the first 911 and third 913 sides and the fourth 915 and sixth 917 sides have opened relative to the flattened tops 901, 903 even more, resulting in the expansion (without substantial foreshortening) of the repeating biphasic cells.

Figure 12:
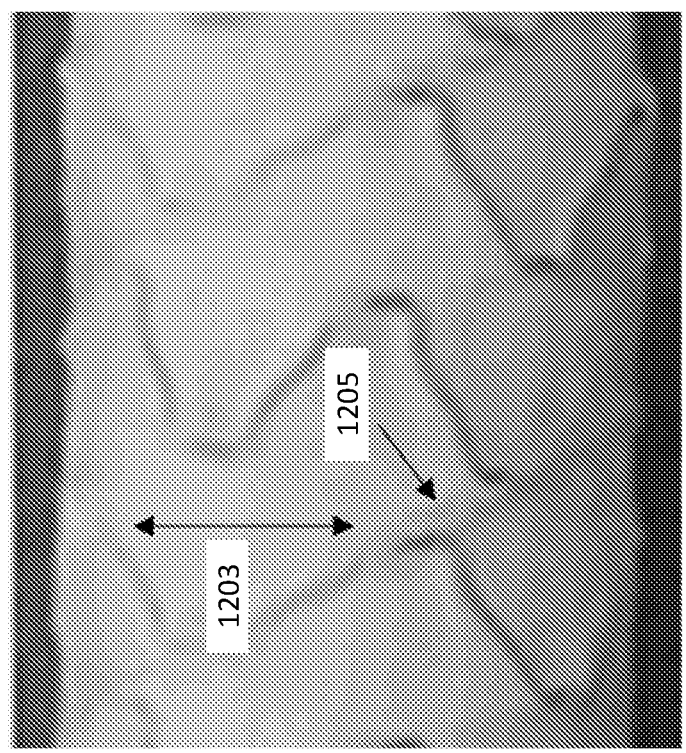
FIG. 12 shows an example of a stent device as described herein in an expanded configuration. In this example, the flat top regions remain flat, and although the unit shapes are foreshortened slightly, this is compensated at least in part by the expansion of the omega-shaped crosslinks.
Figure 11:
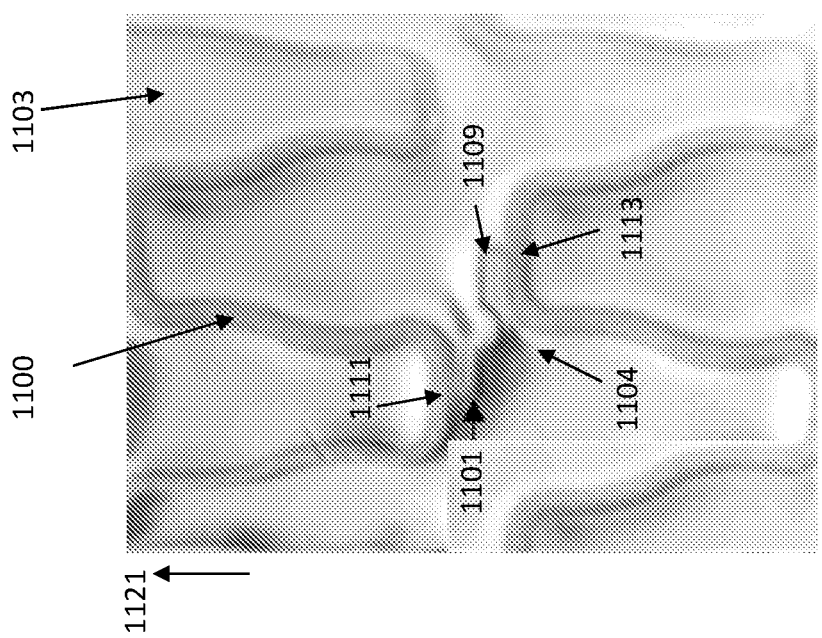
FIG. 11 illustrates one example of a portion of two rings of an exemplary stent apparatus including an omega-shaped crosslink that may be used to join the rings of repeated biphasic shapes (open trapezoidal shapes) forming the stent. Adjacent rings may be interconnected through two (or in some variations, more) crosslinks placed between peaks between adjacent rings.

FIGS. 11 and 12 illustrate an example of a stent device similar to those described above. In FIG. 11, a portion of a stent frame 1100 encapsulated in a sleeve 1103 is shown. The frame is in an un-expanded configuration. FIG. 11 shows an omega-shaped connector 1104 connected via an L-shaped connector 1101 to a flattened top of a first open trapezoidal portion 1111 having a distal-facing opening (the distal direction 1121 is 'up' in FIG. 11). The opposite end of the omega-shaped connector 1109 is a second L-shaped connector (e.g., a right-angled connector) that is connected to a flattened top of another open trapezoidal portion 1113 having a proximal-facing opening on an adjacent ring of the stent.

A stent such as the one shown in FIG. 11 is shown in an expanded view in FIG. 12. In this example, similar to that shown in FIG. 9C, above, the stent frame 1200 is expanded so that the sides of the open trapezoidal portions forming the distal- and proximal-facing openings are spread further apart and the angle between the interconnecting intermediate regions and the flattened top regions is larger, while the flattened top regions remain parallel, and essentially unchanged from the un-expanded configuration. In FIG. 12, the distance between the flattened ends 1203 is much larger than in the un-expanded configuration. The omega-shaped connector(s) 1205 continue to connect the adjacent rings together, while bending to minimize foreshortening of the stent, even when the diameter of the stent increases more than twice its un-expanded diameter.

As described above, the rings forming the stent are interconnected through the omega-shaped crosslinks that build up the stent. Every cylindrical ring may be connected to another cylindrical ring through two crosslinks. The crosslinks may be placed every two connections points, as shown in FIG. 1A-1F, above. The crosslinks are not typically placed on the same connection point as the adjacent rings, but (as shown) may repeat the pattern every other ring. The omega shape may give the stent flexibility when it has to expand. For example, the crosslinks design may allow them to be embedded in a material (e.g., ePTFE) as well as to be crimped and uniformly expanded without ruptures. This type of crosslinks may allow the stent to crimp in the catheter without overlapping each other. As will be described below in FIGS. 16A-16B, the rings may not overlap when the stent is compressed and/or bent in the catheter. The crosslinks may be identical and may have the same organization (orientation) along the stent's length. The stent can be compressed to a diameter that is smaller than the one it was designed in, in order to be placed correctly on the balloon, to obtain a thin profile when placed on the catheter and/or to avoid the stent migration when introduced in the tortuous paths of the vascular vessels.

Thus, in some variations, the membrane, together with the repeating biphasic cell pattern that forms the stent, may make the stent flexible, and the crosslinks position may improve the stent's flexibility, giving a uniform flexibility in the whole structure when the stent graft is bent or kinked. The uniform flexibility may be assisted by the sleeve (e.g., membrane) and the link between the rings through the omega-shaped connectors (crosslinks).

Figure 14A:
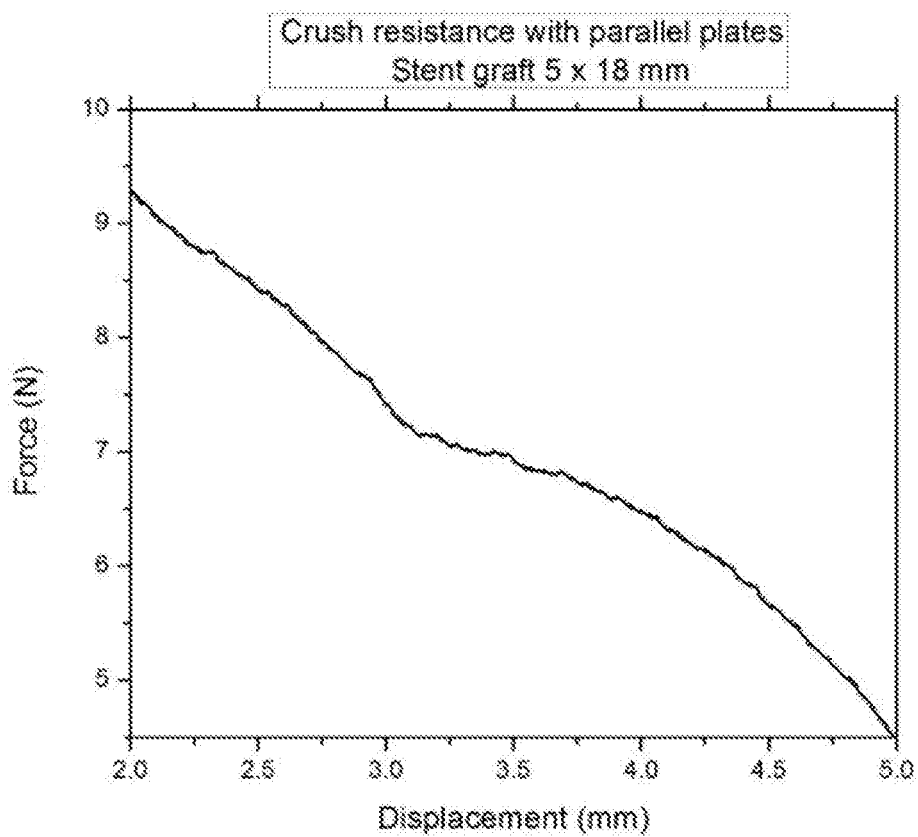
FIG. 14A is a graph showing an example of crush with parallel plates (radial compression) for an example of a stent apparatus as described herein (forcexdisplacement), showing the compression at 50% of the diameter of the stent of about 7.5 N.
Figure 14B:
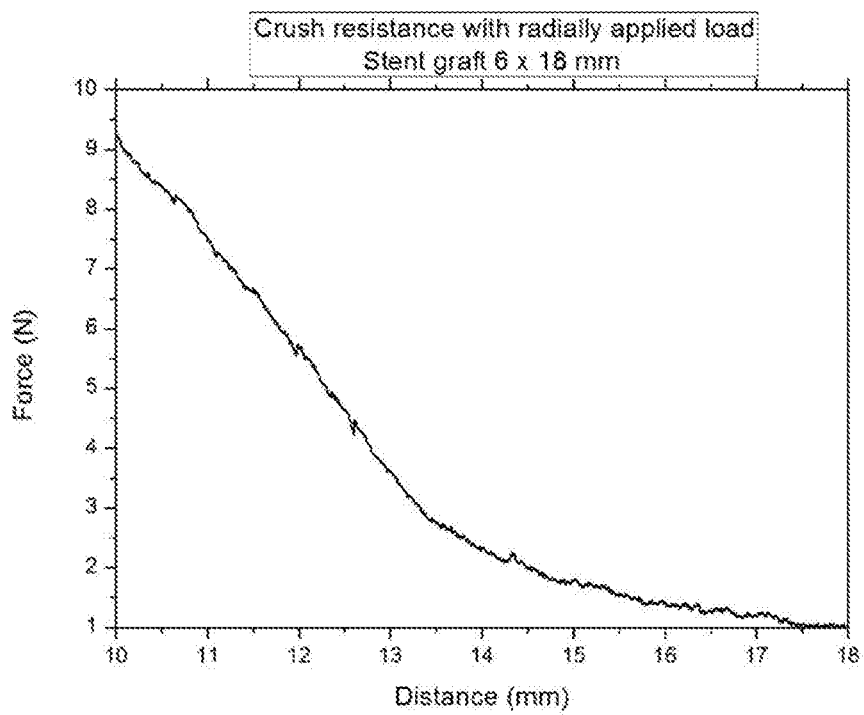
FIG. 14B is a graph showing an example of crush resistance for an example of a stent apparatus with radially applied loads for an example of a stent apparatus as described herein (force×distance).

The stent devices described herein are highly flexible, and may be bent over a tight radius of bending without kinking. For example, FIGS. 14A and 14B illustrate the resistance to crushing of these stents. In FIG. 14A, the graph illustrates compression at 50% of the diameter of the stent, which occurs when a force of about 7.5 N is applied. The test shown in FIG. 14A was performed until the stent was compressed approximately 50% of its length. As shown in FIG. 14B, the maximum force reached was about 9.5 N.

Figure 15A:
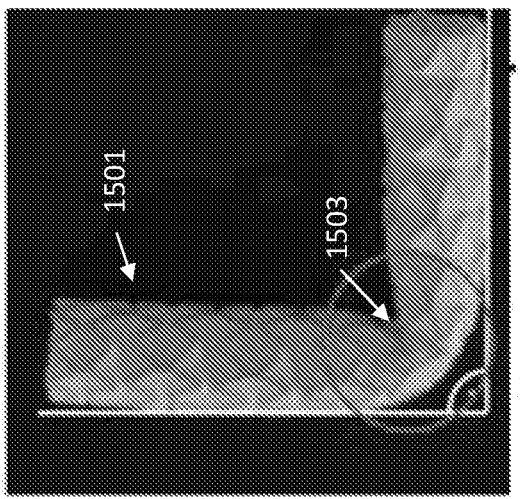
FIGS. 15A-15C illustrate examples of prior art stents showing kinking during bending at 90 degrees.
Figure 15B:
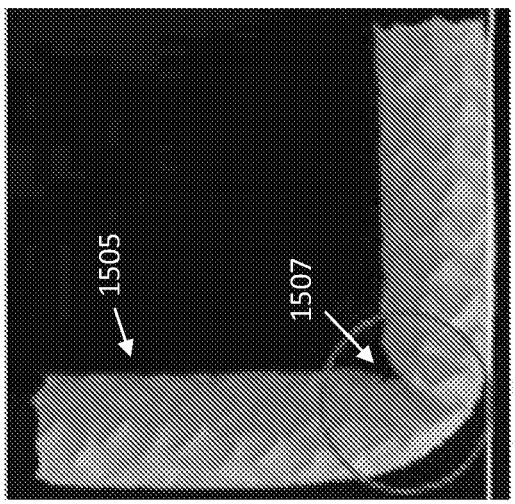
Figure 15C:
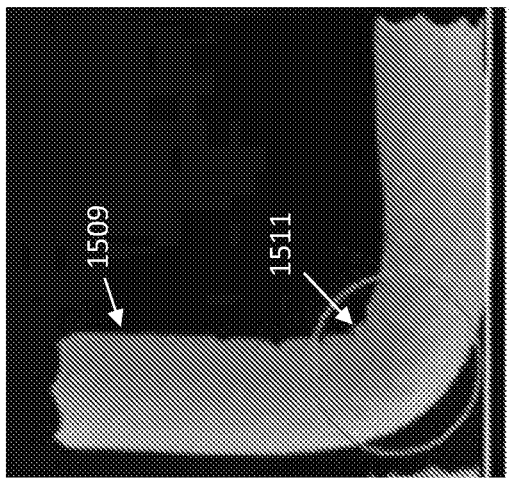

The mechanical properties, including the flexibility and resistance to kinking, was apparent when compared to other prior art stents having similar dimensions. For example, FIG. 15A-15C illustrate various prior art stents in which the flexibility was examined when bending the stents 90 degrees with a very short radius of bending (bending at almost a right angle). For example, FIG. 15A shows bending of a first prior art stent 1501, showing an 8×58 mm stent ("LifeStream" covered stent by CR Bard, having a sinusoidal stent pattern with an offset connector between adjacent rows of sinusoids). This stent kinked 1503 at tight bend radius, as shown. Similarly, FIG. 15, showing an 8×59 mm prior art stent 1505 ("Advanta V12" covered stent by Getinge is a PTFE covered stent having an open cell pattern of adjacent zig-zags interconnected by longitudinal links); this stent also kinked 1507. The prior art stent 1509 in FIG. 15C ("BeGraft" covered stent by Bentley, having a repeating pattern of curly bracket-shapes) also kinked 1511, though less than the devices in FIGS. 15A and 15B.

Figure 16A:
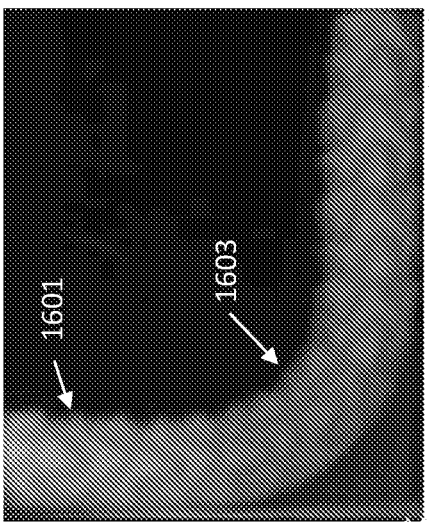
FIGS. 16A and 16B illustrate examples of the stent apparatuses described herein in 90 degree bending, showing smooth (unkinked) bending over the same experimental parameters as the prior art stents shown in FIGS. 15A-15C.
Figure 16B:
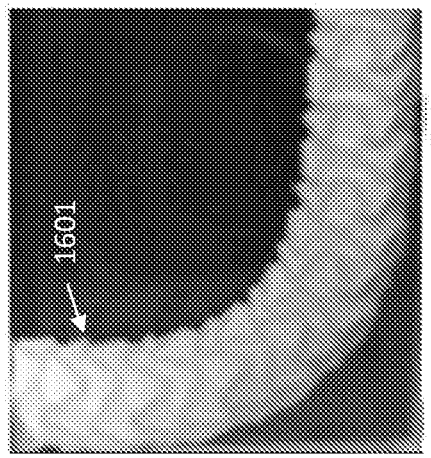

In contrast the stent devices described herein do no appreciably kink. For example a covered stent device having a plurality of adjacent rings arranged transverse to a length of the device, wherein each ring is a ring comprising length of material arranged radially around the length of the stent device as a plurality of repeating biphasic cells, as described above, when bent 90 degrees over the same bend radius did not kink, as shown in FIGS. 16A and 16B. In FIG. 16A, the 5×38 mm stent 1601 did not kink at the bend 1603, in contrast to the prior art devices. Similar result were seen with a 6×38 mm stent 1605, as shown in FIG. 16B.

Figure 17A:
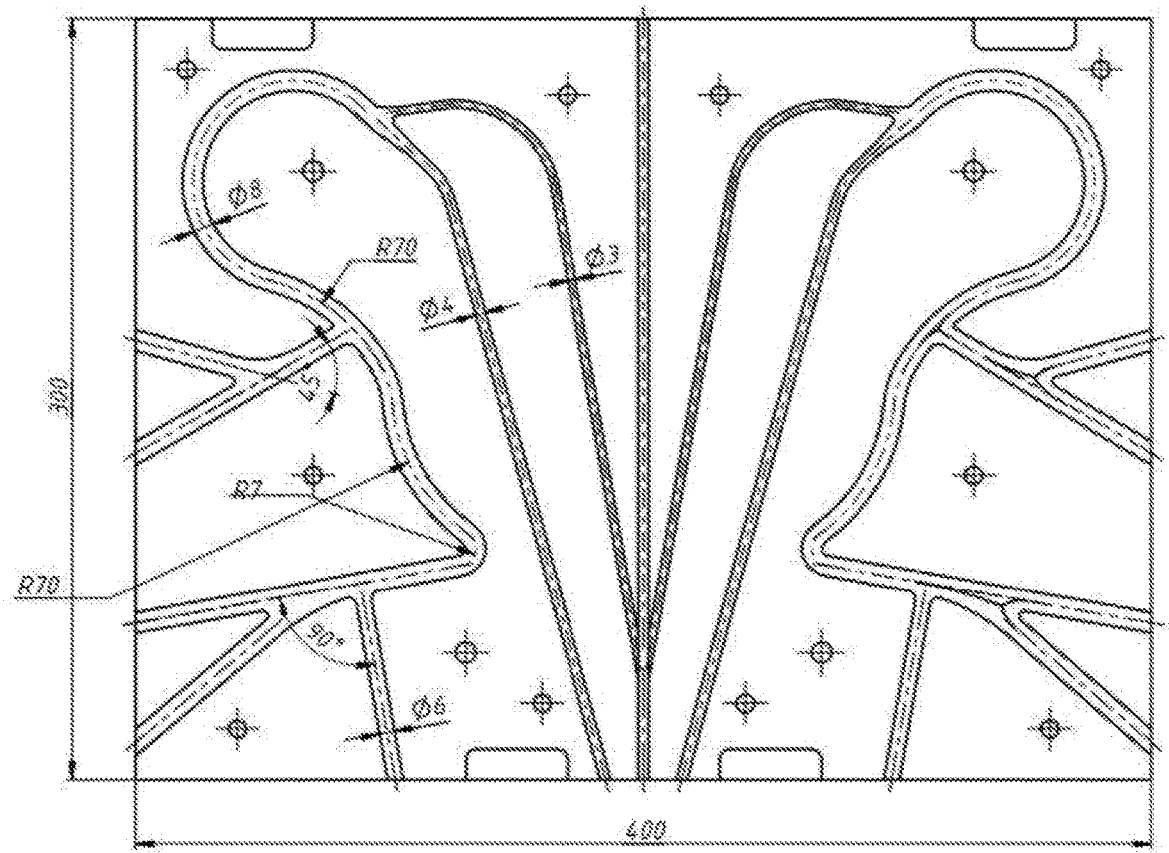
FIG. 17A illustrates an example of a navigability test jig that may be used to characterize a stent apparatus as described herein, having regions ("arteries" of 3, 4, 6 and 8 mm diameters, at angles of between 30-90 degrees and various radius of curvatures.
Figure 17B:
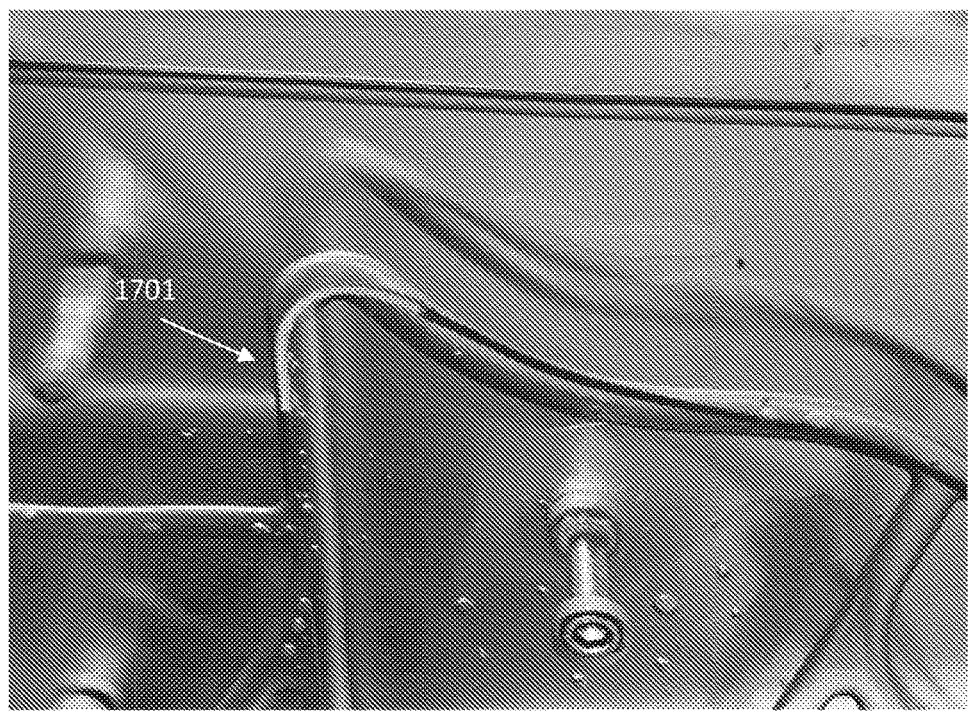
FIG. 17B is an example of one variation of a stent apparatus as described herein shown navigating a test jig such as the one shown in FIG. 17A.

Because the stents described herein also have both a high flexibility, high resilience and a high resistance to kinking, these stents are highly navigable, able to navigate even the most tortuous vessels. Navigability testing was performed on the exemplary stent devices described herein. The navigability test consists of introducing a catheter with the stent covered with ePTFE in a device that simulates the peripheral arterial vasculature, such as the device ("jig") shown schematically in FIG. 17A. The test was performed by a physician specialized in stenting technique. The result of the tests is qualitative, but showed extremely high degrees of navigability and flexibility. The devices described herein were successfully deployed in vessels having diameters of between 3-8 mm (e.g., 3, 4, 6 and 8 mm respectively). For example, FIG. 17B shows an example of a navigability test in which a catheter including a stent 1701 was navigated through a tortious model of a vessel relatively easily. The model used has more complex trajectories than typical peripheral human anatomy. A catheter with a stent graft was navigated smoothly through the device, including through regions of high tortuosity without damage and remained positioned in the catheter. The stent graft has adequate flexibility to traverse complex trajectories, including 30 degree, 45 degree, 60 degree and 90 degree bends.

In general, the stents described herein may be any appropriate size (e.g., unexpanded diameter, expanded diameter, and length). The configuration of repeating biphasic cells and omega-shaped connectors described herein may be particularly well suited for smaller diameter (e.g., 7 m or less) and/or smaller length (e.g., 40 mm or shorter) devices. FIGS. 18A-18D each provide example parameters for four different examples of stents as described herein. All of these exemplary stents were made as covered stents, with an ePTFE sheath (in this case the sheath encapsulated the stent frame as described above). For example, FIG. 18A describes a 5×18 mm stent graft having an initial (unexpanded) diameter of 2.1 mm and final (30 seconds after removal of the balloon) diameter of 5.0 mm. FIG. 18B describes a similar 5×38 mm device, having a starting diameter of about 2.2 mm and a final (30 seconds after removal of the balloon) of about 4.9 mm. FIG. 18C shows an example of a 6×18 mm stent, and FIG. 18D shows an example of a 6×38 mm stent device. In general, all of these devices went from an unexpanded configuration to an expanded configuration of greater than 2×the unexpanded configuration yet had less than 7% foreshortening (e.g., less than 6.5%, less than 6%, less than 5.5%, etc.).

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the disclosure. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/− 0.1% of the stated value (or range of values), +/− 1% of the stated value (or range of values), +/− 2% of the stated value (or range of values), +/− 5% of the stated value (or range of values), +/− 10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the disclosure as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A stent device, the stent device comprising:
   a plurality of adjacent rings arranged transverse to a length of the device in a proximal to distal direction, wherein each ring comprises a length of material arranged radially around the length of the device in a repeating pattern of alternating flattened tops and flattened bottoms, wherein the flattened tops extend transverse to the length of the device and wherein the flattened bottoms extend transverse to the length of the device and further wherein the flattened tops and flattened bottoms are connected by sigmoid-shaped connectors so that each flattened top forms part of a distal-facing U-shape and each flattened bottom forms part of a proximal-facing U-shape;
   a plurality of omega-shaped connectors connecting each ring that is adjacent to a more distal ring to the more distal ring, wherein each omega-shaped connector connects one of the flattened tops of the ring that is adjacent to the more distal ring to one of the flattened bottom of the more distal ring, wherein an omega-shape of each of the omega-shaped connectors connecting the plurality of adjacent rings is oriented in the same proximal to distal direction;
   wherein the stent device has a first configuration in which the plurality of adjacent rings have a first diameter, and the stent device has a second configuration in which the plurality of adjacent rings have a second diameter that is greater than the first diameter, and wherein the flattened tops and the flattened bottoms remain parallel to each other as the stent device is expanded from the first configuration to the second configuration.

2. The device of claim 1, wherein the flattened tops of each ring are radially offset from the flattened bottoms with the same ring.

3. The device of claim 2, wherein the radial offset increases as the stent device transitions from the first configuration to the second configuration.

4. A stent device having a length extending in a distal to proximal direction, the device comprising:
   a plurality of adjacent rings arranged transverse to the length of the device, wherein each ring is a ring comprising a length of material arranged radially around the length of the device as a plurality of repeating biphasic cells, each biphasic cell comprising a first open trapezoidal portion having a first side, a second side and a third side forming a proximal-facing opening, and a second open trapezoidal portion having a fourth side, a fifth side and a sixth side forming a distal-facing opening, wherein the second side and the fifth side are parallel, further wherein the third side of the first open trapezoidal portion is connected to the fourth side of the second open trapezoidal portion by a first connector region extending at a first angle relative to the third side, and wherein the first side of the first open trapezoidal portion connects to a sixth side of an adjacent biphasic cell in the ring by a second connector extending at a second angle relative to the first side; and
   a plurality of omega-shaped connectors connecting each ring that is adjacent to a more distal ring to the more distal ring, wherein each omega-shaped connector connects the second side of one of the first open trapezoidal portions of the plurality of biphasic cells in the ring that is adjacent to the more distal ring to the fifth side of one of the second open trapezoidal portions of the plurality of biphasic cells of the more distal ring wherein each omega connector comprise a first an L-shaped end connecting to the second side of one of the first open trapezoidal portions of the plurality of biphasic cells and a second L-shaped end connecting to the fifth side of one of the second open trapezoidal portions of the plurality of biphasic cells;
   wherein the stent device has a first configuration in which the plurality of adjacent rings have a first diameter, and the stent device has a second configuration in which the plurality of adjacent rings have a second diameter that is greater than the first diameter, and wherein the second side and the fifth side remain parallel as the stent device is expanded from the first configuration to the second configuration.

5. The device of claim 4, wherein the plurality of omega-shaped connectors comprises between 1 and 3 omega-shaped connectors.

6. The device of claim 4, wherein the first open trapezoidal portion of each biphasic cell is radially offset from the second open trapezoidal portion of the same biphasic cell.

7. The device of claim 6, wherein the radial offset between the first open trapezoidal portion and the second open trapezoidal portion increases as the stent device transitions from the first configuration to the second configuration.

8. The device of claim 4, wherein the length of the device is between about 10 mm and about 40 mm.

9. The device of claim 4, wherein the length of material comprises one or more of: an alloy of chromium cobalt, a nickel titanium alloy, a stainless steel and a magnesium alloy.

10. The device of claim 4, further comprising a sleeve comprising a polymeric matrix in which the plurality of rings are encapsulated.

11. The device of claim 4, further wherein an omega-shape of each of the omega-shaped connectors connecting the plurality of adjacent rings is oriented in the same distal to proximal direction.

12. The device of claim 4, wherein the first open trapezoidal portion is an open rectangle.

13. The device of claim 4, wherein the second open trapezoidal portion is an open isosceles trapezoid.

14. The device of claim 4, wherein the first and third sides are parallel and wherein the fourth and sixth sides are not parallel.

15. The device of claim 4, wherein the stent device may bend at least 90 degrees along its length in the first configuration without kinking.

16. The device of claim 4, wherein the device foreshortens less than 7% when expanding from the first configuration to the second configuration.

17. The device of claim 4, wherein the device foreshortens less than 7% when the second diameter of the plurality of adjacent rings is greater than 2.9 times the first diameter of the plurality of adjacent rings.

18. The device of claim 4, wherein the first open trapezoidal portions of the repeating biphasic cells in each of the adjacent rings are aligned along the proximal to distal length of the device.

19. The device of claim 4, wherein each omega-shaped connector includes an arc region and a pair of linear sections extending from the arc regions on either side of the arc region.

20. A stent device having a length extending in a distal to proximal direction, the device comprising:

a plurality of adjacent rings arranged transverse to the length of the device, wherein each ring is a ring comprising a length of material arranged radially around the length of the device as a plurality of repeating biphasic cells, each biphasic cell comprising a first open trapezoidal portion having a first side, a second side and a third side forming a proximal-facing opening, and a second open trapezoidal portion having a fourth side, a fifth side and a sixth side forming a distal-facing opening, wherein the second side and the fifth side are parallel, further wherein the first open trapezoidal portion is radially offset from the second open trapezoidal portion and the third side of the first open trapezoidal portion is connected to the fourth side of the second open trapezoidal portion by a first connector region extending at a first angle relative to the third side, and wherein the first side of the first open trapezoidal portion connects to a sixth side of an adjacent biphasic cell in the ring by a second connector extending at a second angle relative to the first side; and between one and three omega-shaped connectors connecting each ring that is adjacent to a more distal ring to the more distal ring, wherein each omega-shaped connector connects the second side of one of the first open trapezoidal portions of the plurality of biphasic cells in the ring that is adjacent to the more distal ring to the fifth side of one of the second open trapezoidal portions of the plurality of biphasic cells of the more distal ring, further wherein an omega-shape of each of the omega-shaped connectors connecting the plurality of adjacent rings is oriented in the same distal to proximal direction;

wherein the stent device has a first configuration in which a first diameter of the plurality of adjacent rings is between 0.5 mm and 4 mm and a second configuration in which a second diameter of the plurality of adjacent rings is between 3 mm and 7 mm, and wherein the second side and the fifth side remain parallel but the first and second angles change as the stent device expands from the first configuration to the second configuration.

* * * * *